United States Patent
Kupfer

(10) Patent No.: US 9,387,249 B2
(45) Date of Patent: Jul. 12, 2016

(54) METHODS OF TREATING HYPERTENSION WITH AT LEAST ONE ANGIOTENSIN II RECEPTOR BLOCKER AND CHLORTHALIDONE

(75) Inventor: Stuart R. Kupfer, Deerfield, IL (US)

(73) Assignee: Takeda Pharmaceutical Company Limited, Osaka (JP)

( * ) Notice: Subject to any disclaimer, the term of this patent is extended or adjusted under 35 U.S.C. 154(b) by 556 days.

(21) Appl. No.: 12/644,025

(22) Filed: Dec. 22, 2009

(65) Prior Publication Data

US 2010/0204252 A1    Aug. 12, 2010

Related U.S. Application Data

(60) Provisional application No. 61/140,281, filed on Dec. 23, 2008.

(51) Int. Cl.
| | |
|---|---|
| *A61K 45/06* | (2006.01) |
| *A61K 31/404* | (2006.01) |
| *A61K 31/41* | (2006.01) |
| *A61K 31/4184* | (2006.01) |
| *A61K 31/4245* | (2006.01) |

(52) U.S. Cl.
CPC ............. *A61K 45/06* (2013.01); *A61K 31/404* (2013.01); *A61K 31/41* (2013.01); *A61K 31/4184* (2013.01); *A61K 31/4245* (2013.01)

(58) Field of Classification Search
CPC . A61K 2300/00; A61K 31/404; A61K 31/41; A61K 31/4184; A61K 31/4245; A61K 45/06
See application file for complete search history.

(56) References Cited

U.S. PATENT DOCUMENTS

| | | | |
|---|---|---|---|
| 4,514,407 A | * | 4/1985 | Hester et al. ............... 514/220 |
| 5,736,555 A | | 4/1998 | Naka et al. |
| 7,157,584 B2 | | 1/2007 | Kuroita et al. |

FOREIGN PATENT DOCUMENTS

| | | |
|---|---|---|
| EP | 0628313 A1 | 12/1994 |
| EP | 1275391 A1 | 1/2003 |
| WO | 03/059327 A1 | 7/2003 |
| WO | 2004/062729 A1 | 7/2004 |
| WO | 2005/014043 A1 | 2/2005 |
| WO | 2007/019448 A2 | 2/2007 |
| WO | 2009/115301 A1 | 9/2009 |
| WO | 2010/013835 A2 | 2/2010 |

OTHER PUBLICATIONS

Madi, J.C. et al., "Valsartan alone and as part of combination therapy in general practice in Brazil", International Journal of Clinical Practice, vol. 55, No. 8, 2001, pp. 520-523.

Shah, S.U., et al., "Use of diuretics in cardiovascular disease: (2) Hypertension", Postgraduate Medical Journal, McMillan Press, vol. 80, No. 943, Jan. 1, 2004, pp. 271-276.

Smith, R.E., et al., "Antihypertensive therapies", Nature Reviews Drug Discovery, vol. 6, No. 8, Aug. 2007, pp. 597-598.

* cited by examiner

*Primary Examiner* — Sreeni Padmanabhan
*Assistant Examiner* — Jody Karol
(74) *Attorney, Agent, or Firm* — Lisa V. Mueller; Michael Best & Friedrich LLP

(57) ABSTRACT

The present invention relates to a method of treating hypertension in a subject or patient needing treatment thereof by administering to said subject or patient at least one angiotensin II receptor blocker in combination with chlorthalidone.

7 Claims, No Drawings

METHODS OF TREATING HYPERTENSION WITH AT LEAST ONE ANGIOTENSIN II RECEPTOR BLOCKER AND CHLORTHALIDONE

RELATED APPLICATION INFORMATION

This application claims priority to U.S. Application No. 61/140,281 filed on Dec. 23, 2008, the contents of which are herein incorporated by reference.

FIELD OF THE INVENTION

The present invention relates to a method of treating hypertension in a subject or patient needing treatment thereof by administering to said subject or patient at least one angiotensin II receptor blocker in combination with chlorthalidone.

BACKGROUND OF THE INVENTION

Blood pressure (hereinafter referred to as "BP") is defined by a number of haemodynamic parameters taken either in isolation or in combination. Systolic blood pressure (hereinafter referred to as "SBP") is the peak pressure exerted on the walls of the arteries during the contraction phase of the ventricles of the heart. Diastolic blood pressure (hereinafter referred to as "DBP") is the minimum pressure exerted on the vessel walls when the heart muscle relaxes between beats and is filling with blood. The mean arterial blood pressure is the product of cardiac out put and peripheral vascular resistance.

Pre-hypertension has been defined as a SBP in the range of from 120 mmHg to 139 mmHG and/or a DBP in the range of from 80 mmHg to 89 mmHg. Pre-hypertension is considered to be a precursor of hypertension and a predictor of excessive cardiovascular risk (Julius, S., et al., *N. Engl. J. Med.,* 354: 1685-1697 (2006)).

Hypertension, or elevated BP, has been defined as a SBP of at least 140 mmHg and/or a DBP of at least 90 mmHg. By this definition, the prevalence of hypertension in developed countries is about 20% of the adult population, rising to about 60-70% of those aged 60 or more, although a significant fraction of these hypertensive subjects have normal BP when this is measured in a non-clinical setting. Hypertension in individuals with diabetes or renal impairment has been defined as a SBP of at least 130 mmHg and/or a DBP of at least 80 mmHg. Some 60% of this older hypertensive population have isolated systolic hypertension, i.e. they have an elevated SBP and a normal DBP. Hypertension is associated with an increased risk of cardiovascular death, stroke, myocardial infarction, atrial fibrillation, heart failure, peripheral vascular disease and renal impairment (Fagard, R. H., *Am. J. Geriatric Cardiology,* 11(1), 23-28 (2002); Brown, M J and Haycock, S; *Drugs,* 59(Suppl 2), 1-12 (2000)).

The pathophysiology of hypertension is the subject of continuing debate. While it is generally agreed that hypertension is the result of an imbalance between cardiac output and peripheral vascular resistance, and that most hypertensive subjects have normal cardiac output and increased peripheral resistance there is uncertainty which parameter changes first (Beevers, G et al., *BMJ,* 322, 912-916 (2001)).

Chlorthalidone, also known as, benzenesulfonamide, 2-chloro-5-(2,3-dihydro-1-hydroxy-3-oxo-1H-isoindol-1yl) or 2-chloro-5-(1-hydroxy-3-oxo-1,2-dihydroisoindol-1-yl)-benzenesulfonamide, is a long-acting diuretic. Chlorthalidone is an effective treatment to lower elevated arterial blood pressure (arterial hypertension). U.S. Pat. No. 3,055,904 discloses daily doses of chlorthalidone in the amount of 50 mg to 200 mg orally one to three times a day or 100 mg every second day for use as a diuretic. U.S. Pat. No. 5,948,799 discloses a typical range of chlorthalidone of 6.25-200 mg daily and a preferred range of 12.5 to 100 mg daily for use in the treatment of non-ischemic congestive heart failure in combination with amlodipine and/or digoxin. U.S. Patent Application No. 2007/0004792 discloses a method for the treatment of systemic arterial hypertension, which is based on the oral administration to a patient suffering from systemic arterial hypertension either chlorthalidone alone in the amount of 2.5-10 mg daily, or in combination with another anti-hypertensive agent, such as angiotensin converting enzyme inhibitor, angiotensin receptor blocker, calcium antagonist (calcium channel blocker), aldosterone antagonist, beta blocker, alpha blocker.

Thiazide-type diuretics, which includes chlorthalidone, have been effectively used in long-term monotherapy to lower blood pressure, enhance the efficacy of other antihypertensive agents, and reduce cardiovascular events. (Ernst, M., et al., *N. Engl. J. Med.,* 361:2153-2164 (2009)).

Although used to treat hypertension, chlorthalidone is known to cause a number of side effects. These side effects include, but are not limited to, gastrointestinal system reactions (such as, anorexia, gastric irritation, nausea, vomiting, cramping, diarrhea, constipation, jaundice (such as, intrahepatic cholestatic jaundice), pancreatitis), central nervous system reactions (such as, dizziness, vertigo, paresthesias, headache, xanthopsia), hematologic reactions (such as, leukopenia, agranulocytosis, thrombocytopenia, aplastic anemia), dermatologic-hypersensitivity reactions (such as, purpura, photosensitivity, rash, urticaria, necrotizing angiitis (vasculitis) (cutaneous vasculitis), Lyell's syndrome (toxic epidermal necrolysis), cardiovascular reaction (such as, orthostatic hypotension may occur and may be aggravated by alcohol, barbiturates or narcotics and other adverse reactions (such as, hyperglycemia, glycosuria, hyperuricemia, muscle spasm, weakness, restlessness, impotence, azotemia, hypokalemia, hypercalcemia, and hyponatremia).

Chlorthalidone has been combined with antihypertensive agents for use in the treatment of hypertension. For example, CLOPRES® is a combination of clonidine hydrochloride (a centrally acting antihypertensive agent is a class of drugs that is different than angiotensin II receptor blockers (ARBs)) and chlorthalidone for oral administration in three dosage strengths, 0.1 mg/15 mg, 0.2 mg/15 mg and 0.3 mg/15 mg of clonidine hydrochloride/chlorthalidone, respectively.

Angiotensin II receptor blockers (ARB) specifically antagonize or block the action of angiotensin II type 1 receptors. This results in an inhibition of the physiological action of angiotensin II. Angiotensin II is generated as a part of the renin-angiotensin system, and has a strong hypertensive action. A number of ARBs are known in the art. Examples include, losartan, valsartan, irbesartan, candesartan, telmisartan, eprosartan, tasosartan, zolarsartan, olmesartan, certain benzimidazole derivatives having ARB activity (as defined herein) and certain heterocyclic compounds having ARB activity (as defined herein). Combinations of ARBs and diuretics, such as hydrochlorothiazide (HCTZ), are also known.

For example, WO 2005/014043 discloses bilayer tablets comprising 10-800 mg of an ARB and 6.25-50 mg of chlorthalidone for use in treating hypertension. WO 2005/014043 also discloses bilayer tablets comprising 40, 80 mg of sodium salt of telmisartan and 12.5, 25 mg of chlorthalidone for use in treating hypertension. Furthermore, WO 2005/014043 discloses an amount of ARB in a single dosage form in the range of 10-800 mg. Depending on the ARB used, the preferred ranges disclosed are 150-300 mg (e.g. irbesartan), 60-90 mg (e.g. valsartan or telmisartan), 30-60 mg (e.g. telmisartan or losartan) or 15-30 mg (e.g. candesartan). The particularly preferred ranges are 80-85 mg, 40-45 mg or 20-25 mg. The amount of chlorthalidone in a single dosage form is in the range of 10-15 mg or 20-30 mg, preferably 12-13 mg or 24-26 mg.

PCT/JP2009/063833 discloses a solid preparation comprising 0.1-60 weight percentage of a benzimidazole derivative having a strong angiotensin II receptor antagonistic activity and 0.1-60 weight percentage of chlorthalidone for use in treating hypertension. Also disclosed are preparations comprising 21.34, 42.68, 43.465 and 85.36 mg of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and 6.25, 12.5, 25 mg of chlorthalidone for use in treating hypertension. Additionally, PCT/JP2009/063833 discloses the dose of benzimidazole derivative administered to patients is determined based on age, body weight, general health condition, sex, diet, administration time, clearance rate, combination of drugs and the like, as well as the severity of the disease for which the patient is undergoing treatments. Specifically, daily doses in the amount of about 0.05-500 mg, preferably 0.1-100 mg are disclosed. The dose of a diuretic to patients is determined based on age, body weight, general health condition, sex, diet, administration time, clearance rate, combination of drugs and the like, as well as the severity of the disease for which the patient is undergoing treatments. Specifically, the daily dose of diuretic is, for example, about 12.5-100 mg, preferably 15-50 mg, of chlorthalidone (converted into free form). In the case of hydrochlorothiazide (converted into free form), the daily dose is about 12.5-100 mg, preferably 15-50 mg.

However, there is a need in the art for new combinations and dosing regimens for such ARBs and diuretics that exhibit superior efficacy in treating hypertension and that may also exhibit reduced side effects.

SUMMARY OF THE INVENTION

In one embodiment, the present invention relates to a method of treating hypertension in a patient in need of treatment thereof. The method comprises the step of:

administering to said patient from about 1.0 mg per day to 800 mg per day of at least one angiotensin II receptor blocker and from about 1.0 mg per day to about 100 mg per day of chlorthalidone.

Specifically, in the above method, the amount of chlorthalidone is about 50.0 mg per day. More specifically, in the above method, the amount of chlorthalidone is about 25.0 mg per day. Even more specifically, in the above method, the amount of chlorthalidone is about 12.5 mg per day. Still, yet even more specifically, the amount of chlorthalidone is from about 1.0 mg per day to about 10.0 mg per day. Yet, still even more specifically, the amount of chlorthalidone is about 6.25 mg per day.

The hypertension being treated in the above method can be essential hypertension, secondary hypertension, arterial hypertension, pulmonary arterial hypertension or portal vein hypertension.

The angiotensin II receptor blocker that can be used in the above method can be losartan, valsartan, irbesartan, candesartan, telmisartan, eprosartan, tasosartan, zolarsartan, olmesartan, certain benzimidazole derivatives having ARB activity (as defined herein) or certain heterocyclic compounds having ARB activity and a formula II, formula III or formula IV (as defined herein). The at least one benzimidazole derivative having ARB activity (as defined herein) can be selected from the group consisting of:

(i) a compound represented by formula I;

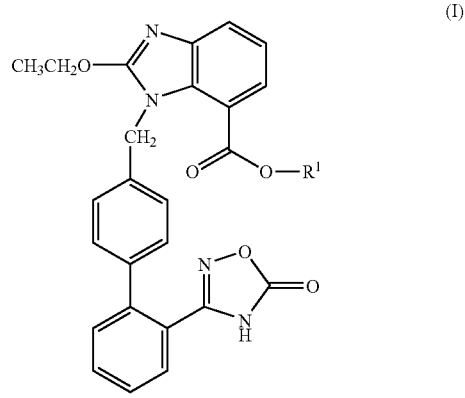

wherein $R^1$ is a group represented by the formula:

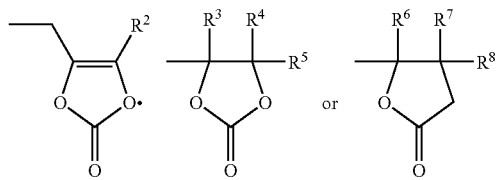

wherein $R^2$, $R^3$, $R^4$, $R^5$, $R^6$, $R^7$ and $R^8$ are each independently a hydrogen atom, a $C_1$-$C_6$ alkyl;

(ii) a salt of the compound of formula (I);

(iii) a compound of formula (I), wherein $R^1$ is a group represented by the below formula:

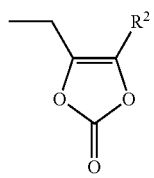

where $R^2$ is as defined above;

(iv) (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate;

(v) 2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate;

(vi) 4-methyl-2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate;

(vii) 5-oxotetrahydro-2-furanyl 2-ethoxy-1-{[2'-(5-oxo-4,5-dihydro-1,2,4-oxadiazol-3-yl)biphenyl-4-yl]methyl}-1H-benzimidazole-7-carboxylate;

(viii) (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt; and (ix) any combinations of (i)-(viii).

Specifically, the benzimidazole derivative (having ARB activity) used in the above method is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt.

An example of a heterocyclic compounds having ARB activity and a formula II, formula III or formula IV is 2-ethoxy-1-[[2'-(2,5-dihydro-5-oxo-1,2,4-oxadiazol-3-yl)biphenyl-4-yl]methyl]benzimidazole-7-carboxylic acid.

In the above method, if a benzimidazole derivative (having ARB activity) is the ARB, then the benzimidazole derivative (having ARB activity) and chlorthalidone are administered as separate dosage forms. For example, in such a method, the benzimidazole derivative (having ARB activity) can be administered as a tablet. Alternatively, in such a method, the chlorthalidone can be administered as a tablet.

In the above method, if a benzimidazole derivative (having ARB activity) is the ARB, then the benzimidazole derivative (having ARB activity) and chlorthalidone can be administered together in a single dosage form. Such a single dosage form can be in the form of a tablet.

DETAILED DESCRIPTION OF THE INVENTION

The present invention relates to methods of treating hypertension in a subject or patient needing treatment thereof. In addition, the methods of the present invention can also be used to prevent cardiovascular event, such as a heart attack, a stroke or cardiovascular death and cardiovascular morbidity and mortality. The methods of the present invention involve administering to a patient in need of treatment at least one angiotensin II receptor blocker in combination with chlorthalidone. Specifically, the at least one angiotensin II receptor blocker can be losartan, valsartan, irbesartan, candesartan, telmisartan, eprosartan, tasosartan, zolarsartan, olmesartan, certain benzimidazole derivatives having ARB activity (defined herein), certain heterocyclic compounds having ARB activity (defined herein) and a formula II, formula III or formula IV as described herein or any combinations thereof. An example of at least one benzimidazole derivative (having ARB activity) that can be used in the methods of the present invention is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt.

Definitions

As used in this specification and the appended claims, the singular forms "a," "an" and "the" include plural references unless the context clearly dictates otherwise. Thus, for example, reference to "an active agent" includes a single active agent as well two or more different active agents in combination.

In describing and claiming the present invention, the following terminology will be used in accordance with the definitions set out below.

The terms "administer", "administering", "administered" or "administration" refer to any manner of providing a drug to a subject or patient. Routes of administration can be accomplished through any means known by those skilled in the art. Such means include, but are not limited to, oral, buccal, intravenous, subcutaneous, intramuscular, by inhalation and the like.

As used herein, the phrases "angiotensin II receptor blocker(s)" or "angiotensin II receptor antagonist(s)" as used herein, refer to agents that antagonize or block the action of, angiotensin II type 1 receptors. Examples of angiotensin II receptor blockers include, but are not limited to, losartan, valsartan, irbesartan, candesartan, telmisartan, eprosartan, tasosartan, zolarsartan, olmesartan, certain benzimidazole derivatives having ARB activity (defined herein) and certain heterocyclic compounds having ARB activity (defined herein) a formula II, formula III or formula IV as described in more detail herein.

Losartan is described in U.S. Pat. Nos. 5,138,069; 5,153,197; 5,210,079; and 5,608,075. It is marketed by Merck & Co., Inc. under the trade names Cozaar® Hyzaar®, Cozaar Plus®. Valsartan is described in U.S. Pat. Nos. 5,399,578 and 6,294,197. It is marketed by Novartis Pharmaceuticals under the trade names Diovan®, Diovan HCT® and Codiovan®. Irbesartan is described in U.S. Pat. Nos. 5,270,317, 6,342,247 and 5,994,348. It is marketed by Bristol Myers Squibb under the trade names Avapro®, Avalide®, Coaprovel® and Karvezide®. Candesartan is described in U.S. Pat. Nos. 5,196,444; 5,534,534; 5,703,110; 5,705,517; 5,721,263 and 5,958,961. It is marketed under by AstraZeneca under the trade names Atacand®, and Atacand HCT®. Telmisartan is described in U.S. Pat. Nos. 5,591,762 and 6,358,986. It is marketed by Boehringer Ingelheim under the trade names Micardis® and Micardis HCT®. Eprosartan is described in U.S. Pat. Nos. 5,185,351 and 5,656,650. It is marketed by Bioval Pharmaceuticals, Inc. under the trade names Teveten® and Teveten HCT®. Olmesartan is described in U.S. Pat. Nos. 5,616,599 and 6,878,703. It is marked by Sankyo and Forest Laboratories under the trade names Benicar® and Benicar® HCT.

As mentioned above, also encompassed within the definition of ARBs are certain heterocyclic compounds having ARB activity and a formula II, formula III or formula IV as shown below:

(a) compounds having a formula II

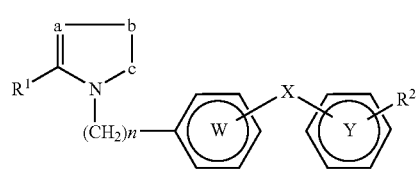

wherein $R_1$ is an optionally substituted hydrocarbon residue which is optionally bonded through a hetero-atom; $R_2$ is an optionally substituted 5-7 membered heterocyclic residue having, as a group capable of constituting the ring, a carbonyl group, a thiocarbonyl group, an optionally oxidized sulfur atom or a group convertible into them; X is a direct bond or a spacer having an atomic length of two or less between the ring Y and the ring W; W and Y are independently an optionally substituted aromatic hydrocarbon residue optionally containing a hetero-atom or an optionally substituted heterocyclic residue; n is an integer of 1 or 2; a and b forming the heterocyclic residue are independently one or two optionally substituted carbon or hetero atoms; c is an optionally substituted carbon or hetero atom; and, in the group of the formula:

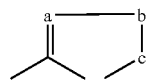

substituents on adjacent two atoms forming the ring are optionally bonded to each other to form a 5-6 membered ring together with the two atoms forming the ring or a salt thereof, (b) compounds having a formula III

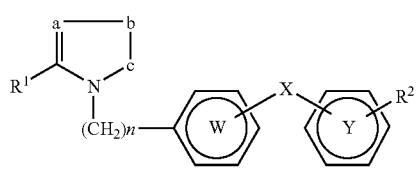

wherein $R_1$ is an optionally substituted hydrocarbon residue which is optionally bonded through a hetero-atom; $R_2$ is an optionally substituted 5-7 membered heterocyclic residue having, as a group capable of constituting the ring, a carbonyl group, a thiocarbonyl group, an optionally oxidized sulfur atom or a group convertible into them; X is a direct bond or a spacer having an atomic length of two or less between the ring Y and the ring W; W and Y are independently an optionally substituted aromatic hydrocarbon residue optionally containing a hetero-atom or an optionally substituted heterocyclic residue; n is an integer of 1 or 2; a and b forming the heterocyclic residue are independently one or two optionally substituted carbon or hetero atoms; c is an optionally substituted carbon or hereto atom; and, when a is an optionally substituted carbon atom, $R_1$ and a may optionally be bonded to each other to form a group of the formula:

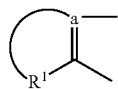

forming a ring or a salt thereof, or
(c) compounds of formula IV:

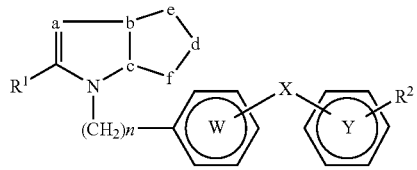

wherein $R_1$ is an optionally substituted hydrocarbon residue which is optionally bonded through a hetero-atom; $R_2$ is an optionally substituted 5-7 membered heterocyclic residue having, as a group capable of constituting the ring, a carbonyl group, a thiocarbonyl group, an optionally oxidized sulfur atom or a group convertible into them; X is a direct bond or a spacer having an atomic length of two or less between the ring Y and the ring W; W and Y are independently an optionally substituted aromatic hydrocarbon residue optionally containing a hetero-atom or an optionally substituted heterocyclic residue; a and e forming the heterocyclic residue are independently one or two optionally substituted carbon or hetero atoms; d and f forming the heterocyclic residue are independently one optionally substituted carbon or hetero atom; b and c are independently one optionally substituted carbon or nitrogen atom; n denotes an integer of 1 or 2; and, when a is an optionally substituted carbon atom, $R_1$ and a may optionally be bonded to each other to form a group of the formula:

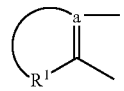

forming a ring or a salt thereof.

The heterocyclic compounds (having ARB activity) described above in (a), (b) and (c) as having formulas II, III and IV respectively are each described in U.S. Pat. No. 5,736, 555, the contents of which are herein incorporated by reference in their entirety. The reader's attention is specifically directed to column 4, beginning at line 39-column 41, line 63, which describes and provides examples of all of the substituents described above as well as methods for making the compounds having the above formulas II, III and IV. An example of a specific heterocyclic compound having one of the above formulas II, III or IV is 2-ethoxy-1-[[2'-(2,5-dihydro-5-oxo-1,2,4-oxadiazol-3-yl)biphenyl-4-yl]methyl]benzimidazole-7-carboxylic acid.

As used herein, the phrase "benzimidazole derivative(s)" or "certain benzimidazole derivatives having ARB activity" refer interchangeably to (i) a compound represented by the below formula I or a salt of a compound of formula I

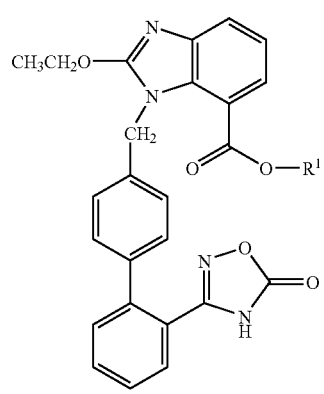

wherein $R^1$ is a group represented by the formula:

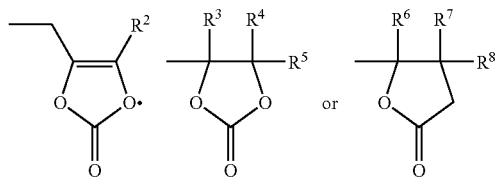

wherein $R^2$, $R^3$, $R^4$, $R^5$, $R^6$, $R^7$ and $R^8$ are each independently a hydrogen atom or a $C_1$-$C_6$ alkyl (such as, for example, methyl, ethyl, n-propyl, isopropyl, n-butyl, isobutyl, sec-butyl, tert-butyl, n-pentyl, isopentyl, neopentyl, n-hexyl, isohexyl, 1,1-dimethylbutyl, 2,2-dimethylbutyl, 3,3-dimethylbutyl, 2-ethylpropyl, etc.);

(ii) a salt of the compound of aforementioned formula (I);
(iii) the compound of aforementioned formula (I), wherein R¹ is a group represented by the below formula:

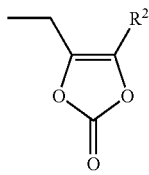

where R² is as defined above;
(iv) a compound selected from the group consisting of: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate, 2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate, 4-methyl-2-oxo-1,3-dioxolan-4-yl 2-ethoxy-1-{[2'-(5-oxo-4,5-dihydro-1,2,4-oxadiazol-3-yl)biphenyl-4-yl]methyl}-1H-benzimidazole-7-carboxylate and 5-oxotetrahydro-2-furanyl 2-ethoxy-1-{[2'-(5-oxo-4,5-dihydro-1,2,4-oxadiazol-3-yl)biphenyl-4-yl]methyl}-1H-benzimidazole-7-carboxylate, or a salt thereof;
(v) (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt;
wherein all of items (i)-(v) are described in U.S. Pat. No. 7,157,584, the contents of which are herein incorporated by reference. Methods and process for making the above compounds are also all described in U.S. Pat. No. 7,157,584.

The term "dosage form" refers to any solid object, semi-solid, or liquid pharmaceutical composition designed to contain a specific pre-determined amount (i.e. dose) of a certain active ingredient (such as a certain benzimidazole derivative having ARB activity (as defined herein), chlorthalidone or a combination of a angiotensin II receptor blocker and chlorthalidone). Suitable dosage forms may be pharmaceutical drug delivery systems, including those for oral administration, buccal administration, rectal administration, topical or mucosal delivery or subcutaneous implants, or other implanted drug delivery systems and the like. Preferably, the dosage form of the pharmaceutical composition of the present invention is considered to be solid; however, they may contain liquid or semi-solid components.

As used herein, the term "essential hypertension" refers to a type of hypertension (e.g., consistently higher then normal blood pressure) wherein no specific medical cause can be found to explain a patient's condition.

The term "patient" refers to an animal, preferably a mammal, including a human or non-human. The terms patient and subject may be used interchangeably herein.

By "pharmaceutically acceptable," such as in the recitation of a "pharmaceutically acceptable excipient," or a "pharmaceutically acceptable additive," is meant a material that is not biologically active or otherwise undesirable, i.e., the material may be incorporated into a pharmaceutical composition administered to a patient without causing any undesirable biological effects.

As used herein, the term "secondary hypertension" refers to a type of hypertension (e.g., consistently higher then normal blood pressure) that is a result of (e.g, secondary to) another condition, such as, but not limited to, kidney disease, tumors, the taking of certain medications, etc The terms "treating" and "treatment" refer to a reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease.

Description Of The Present Invention

The present invention relates to methods of treating hypertension that employ a novel combination and a novel dosing regimen. In addition, the methods of the present invention can also be used to prevent cardiovascular event, such as a heart attack, a stroke or cardiovascular death and cardiovascular morbidity and mortality. More specifically, the methods of the present invention involve administering to a subject or a patient suffering from hypertension and in need of treatment thereof at least one angiotensin II receptor blocker and chlorthalidone. The at least one angiotensin II receptor blocker and chlorthalidone can be co-administered sequentially as separate dosage forms (e.g, such as separate tablets, capsules, a tablet and a capsule, etc.). The order in which the at least one angiotensin II receptor blocker and chlorthalidone can be administered to the patient is not critical. Alternatively, the at least one angiotensin II receptor blocker and chlorthalidone can be combined into a single dosage form for administration to the patient (e.g., such as a tablet, capsule, etc.). Methods for making such a combined dosage form are well known to those skilled in the art. Whether the at least one angiotensin II receptor blocker and chlorthalidone are administered in separate dosage forms or as a single dosage form, said dosage form(s) can contain pharmaceutically acceptable carriers, diluents and/or excipients, which are well known to those in the art.

The amount of the at least one angiotensin II receptor blocker administered to the subject or patient can be from about 1.0 mg per day to about 800 mg per day. More specifically, the amount can be from about 5.0 mg per day to about 500 mg per day. Even more specifically, the amount can be from about 10 mg per day to about 200 mg per day. For example, the amount of at least one angiotensin II receptor blocker that can be administered to the patient is 1.0 mg per day, 2.0 mg per day, 3.0 mg per day, 4.0 mg per day, 5.0 mg per day, 6.0 mg per day, 7.0 mg per day, 8.0 mg per day, 9.0 mg per day, 10 mg per day, 15 mg per day, 20 mg per day, 25 mg per day, 30 mg per day, 35 mg per day, 40 mg per day, 45 mg per day, 50 mg per day, 55 mg per day, 60 mg per day, 65 mg per day, 70 mg per day, 75 mg per day, 80 mg per day, 85 mg per day, 90 mg per day, 95 mg per day, 100 mg per day, 105 mg per day, 110 mg per day, 115 mg per day, 120 mg per day, 125 mg per day, 130 mg per day, 135 mg per day, 140 mg per day, 145 mg per day, 150 mg per day, 155 mg per day, 160 mg per day, 165 mg per day, 170 mg per day, 175 mg per day, 180 mg per day, 185 mg per day, 190 mg per day, 195 mg per day, 200 mg per day, 205 mg per day, 210 mg per day, 215 mg per day, 220 mg per day, 225 mg per day, 230 mg per day, 235 mg per day, 240 mg per day, 245 mg per day, 250 mg per day, 255 mg per day, 260 mg per day, 265 mg per day, 270 mg per day, 275 mg per day, 280 mg per day, 285 mg per day, 290 mg per day, 295 mg per day, 300 mg per day, 305 mg per day, 310 mg per day, 315 mg per day, 320 mg per day, 325 mg per day, 330 mg per day, 335 mg per day, 340 mg per day, 345 mg per day, 350 mg per day, 355 mg per day, 360 mg per day, 365 mg per day, 370 mg per day, 375 mg per day, 380 mg per day, 385 mg per day, 390 mg per day, 395 mg per day, 400 mg per day, 405 mg per day, 410 mg per day, 415 mg per day, 420 mg per day, 425 mg per day, 430 mg per day, 435 mg per day, 440 mg per day, 445 mg per day, 450 mg per day, 455 mg per day, 460 mg per day, 465 mg per day, 470 mg per day, 475 mg per day, 480 mg per day, 485 mg per day, 490 mg per day, 495 mg per day, 500 mg per day, 505 mg per day, 510 mg per day, 515 mg per day, 520 mg per day, 525 mg per day, 530 mg per day, 535 mg per day, 540 mg per day, 545 mg per day, 550 mg per day, 555 mg per day, 560 mg per day, 565 mg per day, 570 mg per day, 575 mg per day, 580 mg per day, 585 mg per day, 590 mg per day, 595 mg per day, 600 mg per day, 605 mg per day, 610 mg per day, 615 mg per day, 620 mg per day, 625 mg per day, 630 mg per day, 635 mg per day, 640 mg per day, 645 mg per day, 650 mg per day, 655 mg per day, 660 mg per day, 665 mg per day, 670 mg per day, 675 mg per day, 680 mg per day, 685 mg per day, 690 mg per day, 695 mg per day, 700 mg per day, 705 mg per day, 710 mg per day, 715 mg per day, 720 mg per day, 725 mg per day, 730 mg per day, 735 mg per day, 740 mg per day, 745 mg per day, 750 mg per day, 755 mg per day, 760 mg per day, 765 mg per day, 770 mg per day, 775 mg per day, 780 mg per day, 785 mg per day, 790 mg per day, 795 mg per day or 800 mg per day. Examples of at least one angiotensin II receptor blocker that can be used are losartan, valsartan, irbesartan, candesartan, telmisartan, eprosartan, tasosartan, zolarsartan, olmesartan, certain benzimidazole derivatives having ARB activity (as defined herein), certain heterocyclic compounds having ARB activity and a formula II, formula III or formula IV (as defined herein) or any combinations thereof. An example of a benzimidazole derivative having ARB activity that can be used in the methods of the present invention is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt.

The amount of chlorthalidone administered to the patient can be from about 1.0 to about 100 mg per day. More specifically, from about 1.0 to about 50.0 mg per day. Even more specifically, the amount of diuretic is from about 1.0 to about 25.0 mg per day. Still, even more specifically, the amount of diuretic is from about 1.0 mg per day to about 10.0 mg per kg per day. For example, the amount of chlorthalidone that can be administered per day is 1.0 mg per day, 1.25 mg per day, 1.5 mg per day, 2.0 mg per day, 2.25 mg per day, 2.5 mg per day, 3.0 mg per day, 3.25 mg per day, 3.5 mg per day, 4.0 mg per day, 4.25 mg per day, 4.5 mg per day, 5.0 mg per day, 5.25 mg per day, 5.5 mg per day, 6.0 mg per day, 6.25 mg per day, 6.5 mg per day, 7.0 mg per day, 7.25 mg per day, 7.5 mg per day, 8.0 mg per day, 8.25 mg per day, 8.5 mg per day, 9.0 mg per day, 9.25 mg per day, 9.5 mg per day, 10.0 mg per day, 10.25 mg per day, 10.5 mg per day, 11.0 mg per day, 11.25 mg per day, 11.5 mg per day, 12.0 mg per day, 12.25 mg per day, 12.5 mg per day, 13.0 mg per day, 13.25 mg per day, 13.5 mg per day, 14.0 mg per day, 14.25 mg per day, 14.5 mg per day, 15.0 mg per day, 15.25 mg per day, 15.5 mg per day, 16.0 mg per day, 16.25 mg per day, 16.5 mg per ay, 17.0 mg per day, 17.25 mg per day, 17.5 mg per day, 18.0 mg per day, 18.25 mg per day, 18.5 mg per day, 19.0 mg per day, 19.25 mg per day, 19.5 mg per day, 20.0 mg per day, 20.25 mg per day, 20.50 mg per day, 21.0 mg per day, 21.25 mg per day, 21.5 mg per day, 22.0 mg per day, 22.25 mg per day, 22.5 mg per day, 23.0 mg per day, 23.25 mg per day, 23.5 mg per day, 24.0 mg per day, 24.25 mg per day, 24.5 mg per day, 25.0 mg per day, 26.25 mg per day, 26.5 mg per day, 27.0 mg per day, 27.25 mg per day, 27.5 mg per ay, 28.0 mg per day, 28.25 mg per day, 28.5 mg per day, 29.0 mg per day, 29.25 mg per day, 29.5 mg per day, 30.0 mg per day, 30.25 mg per day, 30.5 mg per day, 31.0 mg per day, 31.25 mg per day, 31.50 mg per day, 32.0 mg per day, 32.25 mg per day, 32.5 mg per day, 33.0 mg per day, 33.25 mg per day, 33.5 mg per day, 34.0 mg per day, 34.25 mg per day, 34.5 mg per day, 35.0 mg per day, 35.25 mg per day, 35.5 mg per day, 36.0 mg per day, 36.25 mg per day, 36.50 mg per day, 37.0 mg per day, 37.25 mg per day, 37.5 mg per day, 38.0 mg per day, 38.25 mg per day, 38.50 mg per day, 39.0 mg per day, 39.25 mg per day, 39.50 mg per day, 40.0 mg per day, 40.25 mg per day, 40.50 mg per day, 41.0 mg per day, 41.25 mg per day, 41.50 mg per day, 42.0 mg per day, 42.25 mg per day, 42.50 mg per day, 43.0 mg per day, 43.25 mg per day, 43.50 mg per day, 44.0 mg per day, 44.25 mg per day, 44.50 mg per day, 45.0 mg per day, 45.25 mg per day, 45.50 mg per day, 46.0 mg per day, 46.25 mg per day, 46.50 mg per day, 47.0 mg per day, 47.25 mg per day, 47.50 mg per day, 48.0 mg per day, 48.25 mg per day, 48.50 mg per day, 49.0 mg per day, 49.25 mg per day, 49.50 mg per day, 50.0 mg per day, 50.25 mg per day, 50.50 mg per day, 51.0 mg per day, 51.25 mg per day, 51.5 mg per day, 52.0 mg per day, 52.25 mg per day, 52.5 mg per day, 53.0 mg per day, 53.25 mg per day, 53.5 mg per day, 54.0 mg per day, 54.25 mg per day, 54.5 mg per day, 55.0 mg per day, 55.25 mg per day, 55.5 mg per day, 56.0 mg per day, 56.25 mg per day, 56.5 mg per day, 57.0 mg per day, 57.25 mg per day, 57.5 mg per day, 58.0 mg per day, 58.25 mg per day, 58.5 mg per day, 59.0 mg per day, 59.25 mg per day, 59.5 mg per day, 60.0 mg per day, 60.25 mg per day, 60.5 mg per day, 61.0 mg per day, 61.25 mg per day, 61.5 mg per day, 62.0 mg per day, 62.25 mg per day, 62.5 mg per day, 63.0 mg per day, 63.25 mg per day, 63.5 mg per day, 64.0 mg per day, 64.25 mg per day, 64.5 mg per day, 65.0 mg per day, 65.25 mg per day, 65.5 mg per day, 66.0 mg per day, 66.25 mg per day, 66.5 mg per ay, 67.0 mg per day, 67.25 mg per day, 67.5 mg per day, 68.0 mg per day, 68.25 mg per day, 68.5 mg per day, 69.0 mg per day, 69.25 mg per day, 69.5 mg per day, 70.0 mg per day, 70.25 mg per day, 70.50 mg per day, 71.0 mg per day, 71.25 mg per day, 71.5 mg per day, 72.0 mg per day, 72.25 mg per day, 72.5 mg per day, 73.0 mg per day, 73.25 mg per day, 73.5 mg per day, 74.0 mg per day, 74.25 mg per day, 74.5 mg per day, 75.0 mg per day, 76.25 mg per day, 76.5 mg per day, 77.0 mg per day, 77.25 mg per day, 77.5 mg per ay, 78.0 mg per day, 78.25 mg per day, 78.5 mg per day, 79.0 mg per day, 79.25 mg per day, 79.5 mg per day, 80.0 mg per day, 80.25 mg per day, 80.5 mg per day, 81.0 mg per day, 81.25 mg per day, 81.50 mg per day, 82.0 mg per day, 82.25 mg per day, 82.5 mg per day, 83.0 mg per day, 83.25 mg per day, 83.5 mg per day, 84.0 mg per day, 84.25 mg per day, 84.5 mg per day, 85.0 mg per day, 85.25 mg per day, 85.5 mg per day, 86.0 mg per day, 86.25 mg per day, 86.50 mg per day, 87.0 mg per day, 87.25 mg per day, 87.5 mg per day, 88.0 mg per day, 88.25 mg per day, 88.50 mg per day, 89.0 mg per day, 89.25 mg per day, 89.50 mg per day, 90.0 mg per day, 90.25 mg per day, 90.50 mg per day, 91.0 mg per day, 91.25 mg per day, 91.50 mg per day, 92.0 mg per day, 92.25 mg per day, 92.50 mg per day, 93.0 mg per day, 93.25 mg per day, 93.50 mg per day, 94.0 mg per day, 94.25 mg per day, 94.50 mg per day, 95.0 mg per day, 95.25 mg per day, 95.50 mg per day, 96.0 mg per day, 96.25 mg per day, 96.50 mg per day, 97.0 mg per day, 97.25 mg per day, 97.50 mg per day, 98.0 mg per day, 98.25 mg per day, 98.50 mg per day, 99.0 mg per day, 99.25 mg per day, 99.50 mg per day or 100.0 mg per day.

Examples of the amount of at least one ARB and chlorthalidone (either in separate dosage forms or in a single dosage form) that can be administered to a patient in need of treatment thereof pursuant to the methods of the present invention, include, but are not limited to, those shown below in Table A.

TABLE A

| Combination | At least one ARB (mg per day) | Chlorthalidone (mg per day) |
| --- | --- | --- |
| 1 | 80 | 25 |
| 2 | 80 | 12.5 |
| 3 | 40 | 25 |
| 4 | 40 | 12.5 |
| 5 | 20 | 25 |
| 6 | 20 | 12.5 |
| 7 | 80 | 6.25 |
| 8 | 40 | 6.25 |
| 9 | 20 | 6.25 |

A single dosage form containing the at least one ARB and chlorthalidone (also referred to herein as active components) can be made by mixing the respective active components either all together or independently with a physiologically acceptable carrier, excipient, binder, diluent, etc. and administering the mixture or mixtures either orally or non-orally as a pharmaceutical composition. When the active components are formulated independently, the respective formulations can be extemporaneously admixed using a diluent or the like and administered or can be administered independently of each other, either concurrently or at staggered times to the same subject.

The dosage form can be an oral dosage form such as, but not limited to, granules, powders, tablets, capsules, syrups, emulsions, suspensions, etc. and such non-oral dosage forms as injections (e.g. subcutaneous, intravenous, intramuscular and intraperitoneal injections), drip infusions, external application forms (e.g. nasal spray preparations, transdermal preparations, ointments, etc.), and suppositories (e.g. rectal and vaginal suppositories). These dosage forms can be manufactured using routine techniques known in the art. An example of a manufacturing process that can be used is as follows. To manufacture an oral dosage form, an excipient (e.g. lactose, sucrose, starch, mannitol, etc.), a disintegrator (e.g. calcium carbonate, carboxymethylcellulose calcium, etc.), a binder (e.g. α-starch, gum arabic, carboxymethylcellulose, polyvinylpyrrolidone, hydroxypropylcellulose, etc.), and a lubricant (e.g. talc, magnesium stearate, polyethylene glycol 6000, etc.), for instance, are added to the active component or components and the resulting composition is compressed. Where necessary, the compressed product is coated, using routine techniques known in the art, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and Eudragit (Rohm & Haas, Germany, methacrylic-acrylic copolymer).

Injections can be manufactured using routine techniques known in the art. For example, the active components are dissolved, suspended or emulsified in an aqueous vehicle (e.g. distilled water, physiological saline, Ringer's solution, etc.) or an oily vehicle (e.g. vegetable oil such as olive oil, sesame oil, cottonseed oil, corn oil, etc. or propylene glycol) together with a dispersant (e.g. Tween 80 (Atlas Powder, U.S.A.), HCO 60 (Nikko Chemicals), polyethylene glycol, carboxymethylcellulose, sodium alginate, etc.), a preservative (e.g. methyl p-hydroxybenzoate, propyl p-hydroxybenzoate, benzyl alcohol, chlorobutanol, phenol, etc.), an isotonizing agent (e.g. sodium chloride, glycerol, sorbitol, glucose, inverted sugar, etc.) and other additives. If desired, a solubilizer (e.g. sodium salicylate, sodium acetate, etc.), a stabilizer (e.g. human serum albumin), a soothing agent (e.g. benzalkonium chloride, procaine hydrochloride, etc.) and other additives can also be added.

A dosage form for external or topical application can be manufactured by processing the active component or components into a solid, semi-solid or liquid composition. To manufacture a solid composition, for instance, the active component or components, either as they are or in admixture with an excipient (e.g. lactose, mannitol, starch, microcrystalline cellulose, sucrose, etc.), a thickener (e.g. natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g. carbonic acid, phosphoric acid, citric acid, hydrochloric acid, sodium hydroxide, etc.), and a preservative (e.g. p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides (e.g. cacao butter, Witepsols (Dinamit-Nobel), etc.), medium-chain fatty acids (e.g. Migriols (Dinamit-Nobel), etc.), vegetable oils (e.g. sesame oil, soybean oil, cotton-seed oil, etc.), etc. The water-soluble base includes, for instance, polyethylene glycols, propylene glycol, etc. The hydrophilic base includes, for instance, natural gums, cellulose derivatives, vinyl polymers, and acrylic polymers, etc.

The methods of the present invention can be used to treat a subject suffering from any type of hypertension. For example, the methods of the present invention can be used to treat a subject suffering from essential hypertension, secondary hypertension, arterial hypertension, pulmonary arterial hypertension, portal vein hypertension, etc.

The methods of the present invention can also be used to prevent a subject from suffering a cardiovascular event. Examples of cardiovascular events, include, but are not limited to, a heart attack, a stroke or cardiovascular death.

One of the criticisms in the art regarding the use of thiazides, such as chlorthalidone, is their adverse effect profile. Specifically, it is known that thizides can reduce the excretion of calcium and uric acid and therby can cause hypercalcemia and hyperuricemia. Furthermore, thiazide-type diuretics can increase potassium and magnesium excretion, potentially leading to hypokalemia and hypomagnesemia. In addition, studies have found that thiazides causes additional side effects such as new-onset diabetes, attacks of acute gouty arthritis, increases in serum creatine levels, dizziness, muscle cramps, nocturia or incontinence and sun sensitivity. The novel combination of the present invention attenuates one or more of the above mentioned side-effects, including hypokalemia.

By way of example, and not of limitation, examples of the present invention shall now be given.

EXAMPLE 1

A Double-Blind, Randomized, Placebo-Controlled Study to Evaluate the Efficacy and Safety of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt when Co-Administered with Chlorthalidone in Subjects with Essential Hypertension This is a phase 3, multi-center, randomized, parallel group, double-blind, placebo-controlled, study to evaluate the efficacy and safety of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt when combined with chlorthalidone 25 mg once daily (QD) in subjects with uncontrolled essential hypertension.

More specifically, as will be discussed in more detail below, the purpose of this study is evaluate the change in 24-hour mean systolic blood pressure (SBP) by ambulatory blood pressure monitoring (ABPM) in response to (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone compared to placebo plus chlorthalidone for 6 weeks in subjects with uncontrolled essential hypertension. Subjects that qualify for the studied will be discontinued from their current antihypertensive medication. After a 2-week run-in-period, subjects who meet the entry criteria will be given (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone or placebo plus chlorthalidone once daily for 6 weeks. Blood pressure will be monitored during study visits and ABPM will be used to evaluate blood pressure for 24-hour periods twice during the study. Subjects will receive physical examinations including measurement of vital signs and blood and urine samples will be collected (for analyses related to safety monitoring during study visits).

Subject Population: Subjects aged 18 years or older with essential hypertension.
Number of Subjects: Per treatment group: 180; Estimated total: 540
Number of Sites: Approximately 90 sites in the United States and Latin America
Dose Level(s):
 (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt placebo+chlorthalidone 25 mg QD
 (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg+chlorthalidone 25 mg QD
 (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 80 mg+chlorthalidone 25 mg QD
Route of Administration: Oral
Duration of Treatment: Single-Blind Run-In 2 weeks; Double-Blind 6 weeks
Period of Evaluation:
 7 to 14 day Screening Period (washout)
 14 day Placebo Run-In Period
 6 week Double-Blind Treatment
 1-week follow-up for AEs Primary Outcome Measures:
 To evaluate the change in 24-hour mean ABPM SBP in response to (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt (40 mg or 80 mg) compared to placebo for 6 weeks in subjects with essential hypertension when co-administered with chlorthalidone 25 mg.

Secondary Outcome Measures:
 To evaluate change in 24-hour mean ABPM diastolic blood pressure (DBP) in response to (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt compared to placebo when co-administered with chlorthalidone.
 To evaluate the treatment effect of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt on trough, sitting clinic SBP and DBP.
 To evaluate the treatment effect of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt on SBP and DBP using additional ABPM parameters.
 To evaluate the proportion of subjects who achieve response criteria:
  (a) Clinic DBP<90 mmHg.
  (b) Clinic SBP<140 mmHg.
  (a) and (b)
 To evaluate safety and tolerability of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt (Adverse Effects (AEs), safety laboratory tests, vital signs and ECG).

Main Criteria for Inclusion:
1. The subject has essential hypertension (defined as sitting trough clinic SBP between 160 and 190 mm Hg inclusive at Day-1 [day prior to randomization]) and 24-hour mean SBP≥140 mm Hg and ≤180 mm Hg at Day 1.
2. The subject is male or female, aged 18 years or older.
3. The subject is capable of understanding and complying with protocol requirements.
4. The subject or the subject's legally acceptable representative signs a written, informed consent form prior to the initiation of any study procedures.
5. A female subject of childbearing potential who is sexually active agrees to use adequate contraception (as defined in the informed consent form) from screening throughout the duration of the study.
6. The subject has clinical laboratory evaluations (including clinical chemistry, hematology, and complete urinalysis) within the reference range for the testing laboratory or results that are deemed not clinically significant for inclusion into this study by the investigator.
7. The subject is willing to discontinue current antihypertensive medications at the Screening Day-21 visit. If the subject is on amlodipine prior to screening, the subject is willing to discontinue this medication at Screening Day-28.

Main Criteria for Exclusion:
1. The subject has sitting trough clinic diastolic blood pressure (DBP) greater than 119 mmHg at Day-1 (day prior to randomization).
2. The subject has a baseline 24 hour ABPM reading of insufficient quality (as described in the protocol).

3. The subject is taking or expected to take an excluded medication (see Excluded Medication Section).
4. The subject is hypersensitive to Angiotensin II receptor blockers, thiazide-type diuretics, or other sulfonamide-derived compounds.
5. The subject has a recent history (within the last 6 months) of MI, heart failure, unstable angina, coronary artery bypass graft (CABG), percutaneous coronary intervention (PCI), hypertensive encephalopathy, cerebrovascular accident, or transient ischemic attack (TIA).
6. The subject has clinically significant cardiac conduction defects (for example, 3rd degree atrioventricular (AV) block, left bundle branch block (LBBB), sick sinus syndrome, atrial fibrillation).
7. The subject has hemodynamically significant left ventricular outflow obstruction due to aortic valvular disease.
8. The subject has secondary hypertension of any etiology (eg, renovascular disease, pheochromocytoma, Cushing's syndrome).
9. The subject is non-compliant (less than 70% or greater than 130%) with study medication during the placebo run-in period.
10. The subject has severe renal dysfunction or disease (based on calculated creatinine clearance <30 mL/min/1.73 m$^2$) at screening.
11. Subject has known or suspected unilateral or bilateral renal artery stenosis.
12. The subject has a history of drug abuse (defined as illicit drug use) or a history of alcohol abuse (defined as regular or daily consumption of more than 2 alcoholic drinks per day) within the past 2 years.
13. The subject has a previous history of cancer that has not been in remission for at least years prior to the first dose of study drug. (This criterion does not apply to those subjects with basal cell or Stage 1 squamous cell carcinoma of the skin.)
14. The subject has type 1 or poorly controlled type 2 diabetes mellitus (HbA 1c>8.0%).
15. The subject has hypokalemia or hyperkalemia (defined as serum potassium outside of the normal reference range of the central laboratory).
16. The subject has an alanine aminotransferase (ALT) level of greater than 2.5 times the upper limit of normal, active liver disease, or jaundice.
17. The subject has an upper arm circumference less than 24 cm or greater than 42 cm.
18. The subject works night ($3^{rd}$) shift (defined as 11 PM [2300] to 7 AM [0700]).
19. The subject is unwilling or unable to comply with the protocol or scheduled appointments.
20. The subject is unable to understand verbal or written English or any other language for which a certified translation of the approved informed consent is available.
21. If female, the subject is pregnant, intends to become pregnant during the course of the study, or is lactating.
22. The subject currently is participating in another investigational study or has participated in an investigational study within 30 days prior to randomization.
23. The subject is a study site employee, or is an immediate family member (ie, spouse, parent, child, sibling) of a study site employee who is involved in conduct of this study.
24. The subject has any other serious disease or condition at Screening (or Randomization) that would compromise subject safety, might affect life expectancy, or make it difficult to successfully manage and follow the subject according to the protocol.
25. The subject has been randomized in a previous (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt study.

Main Criteria for Evaluation and Analyses:

The primary outcome measured for this study is change from baseline to Week 6 in the 24-hour mean ABPM SBP. The key secondary outcome measured is change from baseline to Week 6 in trough clinic sitting SBP. Other secondary outcomes measured for this study are:

Change from baseline to Week 6 in the 24-hour mean ABPM DBP of (5-methyl-2-oxo-1,3-dioxol-4-yl)methyl 2-ethoxy-1-{[T-(5-oxo-4,5-dihydro-1,2,4-oxadiazol-3-yl)biphenyl-4-yl]methyl}-1H-benzimidazole-7-carboxylate potassium salt and sitting trough clinic DBP of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt.

Change from baseline to Week 6 in systolic and diastolic blood pressure using additional ABPM parameters (daytime mean [6 am to 10 pm], nighttime mean [12 am to 6 am], BP mean at 0-12 hours after dosing, and trough mean at 22 to 24 hours after dosing).

Safety outcomes measured (Adverse Events (AEs), safety laboratory tests, ECGs, and vital signs).

Sample Size Justification: Assuming a 13 mmHg standard deviation, a 15% dropout rate, a total of 540 subjects (180 per treatment group) is sufficient to achieve at least 90% power to detect a difference of 5 mmHg between the active treatment groups and placebo by a 2-sample t-test of the mean change from Baseline in 24-hour mean ABPM SBP with a 0.05 2-sided significance level. Similarly, assuming a standard deviation of 14 mm Hg for mean change from Baseline in trough clinic sitting SBP, the sample size provides at least 85% power to detect a difference of 5 mm Hg in trough clinic sitting SBP between the active treatment groups and placebo with a two-sided significance level of 5%.

Statistical Considerations:

Efficacy Analysis

The primary efficacy variable is change from baseline in the 24-hour mean SBP by ABPM while the key secondary efficacy variable is change from baseline in trough clinic sitting SBP.

The primary analysis will be based on an analysis of covariance (ANCOVA) model for change from Baseline to Week 6 or last on-treatment visit for 24-hour mean ABPM SBP. The model will include treatment baseline 24-hour mean ABPM SBP as covariate. The primary comparison will be performed between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and placebo. The LS mean, p-value and 2-sided 95% confidence interval of treatment difference in change from baseline between (5-methyl-2-oxo-1,3-dioxol-4-yl)methyl 2-ethoxy-1-{[2'-(5-oxo-4,5-dihydro-1,2,4-oxadiazol-3-yl) biphenyl-4-yl]methyl}-1H-benzimidazole-7-carboxylate potassium salt and placebo will be provided. The type 1 error will be controlled for the primary analysis by using the principle of 'closed' testing. Under this principle, each of the pair-wise comparisons will be conducted at the 0.05 level with no p-value adjustments if the hypothesis "all treatment groups equal" is first rejected at the 0.05 level.

Secondary analysis will be performed on change from baseline in 24-hour mean ABPM DBP with treatment as fixed effect and baseline in 24-hour mean ABPM DBP as a covariate. These analyses will also be performed on other ABPM parameters for SBP and DBP, including daytime mean (6 AM to 10 PM), nighttime mean (12 AM to 6 AM), BP mean at 0 to 12 hours after dosing, and trough mean at 22 to 24 hours after dosing.

Similar analyses will be performed on the trough, clinic sitting DBP. Analyses on the clinic DBP and SBP. Analyses on the clinic DBP and SBP will also be conducted at each scheduled visit.

A logistic model with treatment as fixed effect and baseline clinic SBP as a covariate will be used to analyze the response criteria for clinic SBP. The odds ratio and its 95% confidence will be estimated. Similarly, a logistic model with treatment as fixed and baseline clinic DBP as a covariate will be used to analyze the response criteria for clinic DBP. The joint response criteria for both clinic SBP and DBP will be analyzed using a logistic model with treatment as fixed effect and baseline clinic SBP as a covariate.

The efficacy analysis for the clinic DBP and SBP will be based on last-observation-carried-forward (LOCF) data set. In the LOCF analysis data set, the last post-baseline double-blind observed value will be carried forward and used for all subsequent scheduled time points where data are missing (e.g. the subject has missing data or has dropped out of the study). The efficacy analysis for the response criteria will also be based on the LOCF data set. Sensitivity analyses on clinic SBP and DBP will be performed on observed values and using multiple imputation for missing clinic BP data to assess the impact of LOCF methodology and dropout. If there is more than 20% of missing ABPM data, sensitivity analyses on 24-hour mean SBP and DBP by ABPM will be done by assessing clinic SBP and DBP and using multiple imputation for missing ABPM data whenever possible.

Subgroup analyses such as age, gender, race and other important baseline factors may be performed for primary and secondary efficacy variables. Exploratory analyses on region or center effect may be performed for primary and key secondary efficacy variables.

Safety Analysis

Safety evaluation will include adverse events, clinical laboratory data, vital signs, and ECG findings.

EXAMPLE 2

A Phase 3, Double-Blind, Randomized, Factorial, Efficacy and Safety Study of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt Plus Chlorthalidone Fixed-Dose Combination in Subjects with Moderate to Severe Hypertension Purpose This study is being conducted to determine the efficacy and safety of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt combined with chlorthalidone in subjects with moderate to severe hypertension. More specifically, this study is a phase 3, double-blind, randomized, factorial, efficacy and safety study of (5-methyl-2-oxo-1,3-dioxol-4-yl)methyl 2-ethoxy-1-{[2'45-oxo-4,5-dihydro-1,2,4-oxadiazol-3-yl)biphenyl-4-yl]methyl}-1H-benzimidazole-7-carboxylate potassium salt plus chlorthalidone fixed-dose combination in subjects with moderate to severe hypertension.

Number of Subjects: 150 to 165 per treatment group for a total of 1650 to 1815 subjects.

Number of Sites: Approximately 300 sites in United States, Central/South America, Europe, and Russia.

Route of Administration: Oral

Duration of Treatment: 8 weeks

Period of Evaluation: 13 weeks

Primary Outcome Measures:
  Change from baseline to Week 8 in trough, systolic blood pressure as measured by AMPM. [Time Frame: Baseline and Week 8]

Secondary Outcome Measures:
  Change from baseline to Week 8 in trough, sitting, clinic systolic blood pressure. [Time Frame: Baseline and Week 8]
  Change from Baseline to Week 8 in trough, sitting, clinic diastolic blood pressure. [Time Frame: Baseline and Week 8]
  Change from Baseline to Week 8 in the mean trough diastolic blood pressure (22 to 24 hours after dosing), as measured by Ambulatory Blood Pressure Monitoring. [Time Frame: Baseline and Week 8]
  Change from Baseline to Week 8 in the 24-hour mean systolic blood pressure and diastolic blood pressure, as measured by Ambulatory Blood Pressure Monitoring. [Time Frame: Baseline and Week 8]
  Change from Baseline to Week 8 in the mean daytime (6 AM to 10 PM) systolic blood pressure and diastolic blood pressure, as measured by Ambulatory Blood Pressure Monitoring. [Time Frame: Baseline and Week 8]
  Change from Baseline to Week 8 in the mean nighttime (12 AM to 6 AM) systolic blood pressure and diastolic blood pressure, as measured by Ambulatory Blood Pressure Monitoring. [Time Frame: Baseline and Week 8]
  Change from Baseline to Week 8 in the mean systolic blood pressure and diastolic blood pressure at 0 to 12 hours after dosing, as measured by Ambulatory Blood Pressure Monitoring. [Time Frame: Baseline and Week 8]
  Proportion of responders at Week 8, as defined by clinic systolic blood pressure <140 mm Hg and/or a reduction of ≥20 mm Hg from baseline. [Time Frame Baseline and Week 8]
  Proportion of responders at Week 8, as defined by clinic diastolic blood pressure <90 mm Hg and/or a reduction of ≥10 mm Hg from baseline. [Time Frame Baseline and Week 8]
  Proportion of responders at Week 8, as defined by clinic systolic blood pressure <140 mm Hg and/or a reduction of ≥20 mm Hg from baseline AND clinic diastolic blood pressure <90 mm Hg and/or a reduction of ≥10 mm Hg from baseline. [Time Frame: Baseline and Week 8]

| Arms | Assigned Interventions |
|---|---|
| 1: Experimental | Drug: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and chlorthalidone (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 20 mg, tablets, orally, once daily and chlorthalidone 12.5 mg, tablets, orally, once daily for up to 8 weeks |

-continued

| Arms | Assigned Interventions |
|---|---|
| 2: Experimental | Drug: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and chlorthalidone<br>(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]metbyl}-1H-benzimidazole-7-carboxylate potassium salt 20 mg, tablets, orally, once daily and chlorthalidone 25 mg, tablets, orally, once daily for up to 8 weeks |
| 3: Experimental | Drug: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and chlorthalidone<br>(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg, tablets, orally, once daily and chlorthalidone 12.5 mg, tablets, orally, once daily for up to 8 weeks |
| 4: Experimental | Drug: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and chlorthalidone<br>(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg, tablets, orally, once daily and chlorthalidone 25 mg, tablets, orally, once daily for up to 8 weeks |
| 5: Experimental | Drug: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and chlorthalidone<br>(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 80 mg, tablets, orally, once daily and chlorthalidone 12.5 mg, tablets, orally, once daily for up to 8 weeks |
| 6: Experimental | Drug: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and chlorthalidone<br>(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 80 mg, tablets, orally, once daily and chlorthalidone 25 mg, tablets, orally, once daily for up to 8 weeks |
| 7: Active Comparator | Drug: Chlorthalidone<br>(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt placebo-matching tablets, orally, once daily and chlorthalidone 12.5 mg, tablets, orally, once daily for up to 8 weeks |
| 8: Active Comparator | Drug: Chlorthalidone<br>(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt placebo-matching tablets, orally, once daily and chlorthalidone 25 mg, tablets, orally, once daily for up to 8 weeks |
| 9: Experimental | Drug: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt<br>(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 20 mg, tablets, orally, once daily and chlorthalidone placebo-matching tablets, orally, once daily for up to 8 weeks |
| 10: Experimental | Drug: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt<br>(5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg, tablets, orally, once daily and chlorthalidone placebo-matching tablets, orally, once daily for up to 8 weeks |

| Arms | Assigned Interventions |
|---|---|
| 11: Experimental | Drug: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 80 mg, tablets, orally, once daily and chlorthalidone placebo-matching tablets, orally, once daily for up to 8 weeks |

This study was designed to compare the antihypertensive effect and the safety and tolerability of the (5-methyl-2-oxo-1,3-dioxol-4-yl)methyl 2-ethoxy-1-{([2'-(5-oxo-4,5-dihydro-1,2,4-oxadiazol-3-yl)biphenyl-4-yl]methyl}-1H-benzimidazole-7-carboxylate potassium salt plus chlorthalidone (CLD) fixed-dose combination product ((5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD FDC) with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt monotherapy and chlorthalidone monotherapy during 8 weeks of treatment.

Subjects participating in this study were randomized to receive one of 11 possible dosing combinations of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt, chlorthalidone and placebo over an 8 week period. The total duration of the study will be approximately 13 weeks. Subjects are making 12 visits to the clinic. Each subject is also being contacted by telephone 14 days after last dose of study drug for a follow-up assessment. Sitting, trough, clinic blood pressure readings will be made at each visit; mean sitting, clinic a systolic blood pressure of 160 to 190 mm Hg, inclusive, will be required to qualify for study entry. 24-hour ambulatory blood pressure monitoring (ABPM) recordings will be made 3 times during the study: the baseline recording will begin immediately after dosing on the last day of the placebo lead-in period (Day-1). The interim ABPM will take place at Week 4, and the final ABPM recording will begin after administration of the last dose of double-blind treatment at the Week 8 Visit.

Eligibility:

| | |
|---|---|
| Ages Eligible for Study: | 18 Years and older |
| Genders Eligible for Study: | Both |
| Health Volunteers Accepted: | No |

Criteria

Inclusion Criteria

Is 18 years of age or older and is treated with antihypertensive therapy and has a post-washout mean sitting clinic systolic blood pressure greater than or equal to 160 and less than or equal to 190 mm Hg on the day prior to randomization, or the subject has not received antihypertensive treatment within 28 days prior to Screening and has a mean sitting clinic systolic blood pressure greater than or equal to 160 and less than or equal to 190 mm Hg at the Screening Visit and on the day prior to randomization.

Females of childbearing potential who are sexually active must agree to use adequate contraception, and can neither be pregnant nor lactating from Screening throughout the duration of the study.

Has clinical laboratory test results within the reference range for the testing laboratory or the investigator does not consider the results to be clinically significant.

Is willing to discontinue current antihypertensive medications on Day-21 or on Day-28 for a washout period.

Is capable of understanding and willing to comply with the protocol requirements.

Is willing to sign the informed consent prior to undergoing any study related procedures.

Exclusion Criteria

Has a mean sitting clinic diastolic blood pressure greater than 119 mm Hg on the day prior to randomization.

Has works a night (third) shift (defined as 11 PM [2300] to 7 AM [0700]).

Has an upper arm circumference less than 24 cm or greater than 42 cm.

Has secondary hypertension of any etiology.

Has known hypersensitivity to angiotensin II receptor blockers or thiazide-type diuretics.

Has been randomized in a previous (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt study.

As mentioned above, this study was designed to compare the antihypertensive effect and the safety and tolerability of the (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone fixed-dose combination product ((5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD FDC) with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt monotherapy and chlorthalidone monotherapy during 8 weeks of treatment.

Sample Size Justification:

Assuming an SD of 14 mm Hg and a 15% dropout rate, a sample size of 150 subjects per treatment group (total of 1650 subjects) is sufficient to achieve at least 90% power to detect a difference of 4 mm Hg between the combined (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt chlorthalidone treatment groups versus the combined 2 treatment groups of chlorthalidone alone (e.g. (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD 80 mg+12.5 mg and (5-methyl-2-oxo-1,3-dioxol-4-yl)methyl 2-ethoxy-1-{[2'-(5-oxo-4,5- dihydro-1,2,4-oxadiazol-3-yl)biphenyl-4-yl]methyl}-1H-benzimidazole-7-carboxylate potassium salt CLD 80 mg+25 mg treatment groups combined versus (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD P mg+. 12.5 mg and (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD P mg+25 mg treatment groups combined). Likewise, there will be at least 90% power to detect a difference of 4 mm Hg between the combined two (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD treatment groups versus the combined two treatment groups of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt alone (e.g. (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD 80 mg+25 mg and (5-methyl-2-oxo-1,3-dioxol-4-yl)methyl 2-ethoxy-1-{[2'-oxo-4,5-dihydro-1,2,4-oxadiazol-3-yl)biphenyl-4-yl]methyl}-1H-benzimidazole-7-carboxylate potassium salt CLD 40 mg+25 mg treatment groups combined versus (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD 80 mg+P mg and (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD 40 mg+P mg treatment groups combined). Both calculations were performed with a 2-sample t-test on the mean change from baseline to Week 8 in trough SBP as measured by ABPM with an overall 0.05 2-sided significance level. Assuming the same SD and treatment effect of 4 mm Hg for the mean change from baseline to Week 8 in trough clinic sitting SBP, above sample size calculations were also applied for change from baseline in trough clinic sitting SBP.

Statistical Considerations:

The primary endpoint will be change from baseline in trough SBP by ABPM and the key secondary endpoint will be change from baseline in trough, sitting, clinic SBP. Other secondary endpoints will include DBP by ABPM; trough, sitting, clinic DBP; 24-hour mean SBP and DBP by ABPM; other ABPM parameters for SBP and DBP and blood pressure response rates. Trough-to-peak ratio will also be calculated and summarized.

To demonstrate that (5-methyl-2-oxo-1,3-dioxol-4-yl)methyl 2-ethoxy-1-{[2'-oxo-4,5-dihydro-1,2,4-oxadiazol-3-yl)biphenyl-4-yl]methyl}-1H-benzimidazole-7-carboxylate potassium salt CLD FDC is more effective, it is required that there is statistically significant treatment difference on change from baseline to Week 8 in trough SBP by APBM between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD FDC and (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt alone and between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD FDC and chlorthalidone alone. Both comparisons will be performed at 2-sided 5% significant level.

The primary endpoint will be analyzed using an analysis of covariance (ANCOVA) model, with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt doses, chlorthalidone doses as factors and baseline trough SBP by ABPM as a covariate in the model. To demonstrate that the (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD FDC is more effective than chlorthalidone alone, a step down testing procedure in the following sequential order will be used. Since the comparisons will be done sequentially using a step down testing procedure within each step, no adjustment of alpha level will be made for each step. Data from subjects treated with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD 80 mg+12.5 mg and (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD 80 mg+25 mg will be compared with data from subjects who are treated with P mg+12 mg and P mg+25 mg. The ANCOVA model will be applied only to the data from these 4 cells. (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 80 mg vs. placebo will be tested at a significance level of 5% using the least squares (LS) means and SDs obtained from this ANCOVA analysis. If this test is statistically significant, (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 80 mg will be considered to have contributed to the effect of combination treatment and the comparison of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg and placebo will be made using the same testing procedures. If no statistical significant difference between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 80 mg and placebo was observed, no additional comparison will be performed. If there is statistically significant difference between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg and placebo, (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg will be considered to have contributed to the effect of combination treatment and comparison of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 20 mg and placebo will be made using the same testing procedures. If no statistical significant difference between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg and placebo was observed, no additional comparison will be performed.

Similarly, the step-down procedure will be used to demonstrate that (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD FDC is more effective than (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt alone for each of chlorthalidone doses. Data from subjects treated with (5-methyl-2-oxo-1,3-dioxol-4-yl)methyl 2-ethoxy-1-{[2'-(5-oxo-4,5-dihydro-1,2,4'-oxadiazol-3-yl)biphenyl-4-yl]methyl}-1H-benzimidazole-7-carboxylate potassium salt CLD 40 mg+25 mg and (5-methyl-2-oxo-1,3-dioxol-4-yl)methyl 2-ethoxy-1-{[2'45-oxo-4,5-dihydro-1,2,4-oxadiazol-3-yl)biphenyl-4-yl]methyl}-1H-benzimidazole-7-carboxylate potassium salt CLD 80 mg+25 mg will be compared with data from subjects who are treated with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg+P mg and (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt CLD 80 mg+P mg. The ANCOVA model will be applied only to the data from these 4 cells. Chlorthalidone 25 mg versus placebo will be tested at a significance level of 5% using the LS means and SDs obtained from this ANCOVA analysis. If there is statistically significant difference between chlorthalidone 25 mg and placebo, chlorthalidone 25 mg will be considered to have contributed to the effect of combination treatment and the comparison of chlorthalidone 12.5 mg and placebo will be made using the same testing procedures. If no statistical significant difference between chlorthalidone 25 mg and placebo was observed, no additional comparison will be performed.

As the key secondary endpoint, trough sitting clinic SBP will be analyzed in the same fashion. In addition, trough DBP by ABPM and trough sitting clinic DBP will be analyzed similarly as described above.

A secondary analysis of the primary endpoint will also be performed with an ANCOVA analysis with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt dose, chlorthalidone dose as factors and baseline value as covariate using all subjects' data. Furthermore, an interaction term between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt dose and chlorthalidone dose will be added to the above model and tested at a significance level of 5%. Within the framework of the ANCOVA model with the interaction term, cell by cell comparisons for each FDC dose versus either component will be performed at the 5% level of significance. No adjustments will be made for multiple comparisons. Response surface analysis will also be performed. Blood pressure lowering effect in relation to (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and chlorthalidone doses will be characterized by response surface analyses with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and chlorthalidone doses as the basis of predictor variables.

Secondary analysis will be performed on change from baseline in other ABPM parameters and trough sitting clinic SBP and DBP using an ANCOVA model with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt doses, chlorthalidone doses as fixed effects and baseline as a covariate using all subjects' data. Furthermore, an interaction term between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt doses and chlorthalidone doses will be added to the above model and tested at a significance level of 5%. Within the framework of the ANCOVA model with the interaction term, cell by cell comparisons for each FDC dose versus either component will be performed at the 5% level of significance. By visit analysis information will be presented.

A logistic model with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt doses, chlorthalidone doses and an interaction term between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt doses and chlorthalidone doses as fixed effects and baseline SBP as a covariate will be used to analyze the response criteria for clinic SBP. The odds ratio and its 95% confidence interval will be estimated. Similar models will be used to analyze the response criteria for clinic DBP with baseline clinic DBP as a covariate and the joint response criteria for both clinic SBP and DBP with baseline clinic SBP as a covariate.

The efficacy analysis will be based on last-observation-carried-forward (LOCF) data set. In the LOCF analysis data set, the last post-baseline double-blind observed value will be carried forward and used for all subsequent scheduled time points where data are missing (e.g. the subject has missing data or has dropped out of the study). The efficacy analysis for the response criteria will also be based on the LOCF data set. Sensitivity analyses on trough SBP and DP will be performed on observed values and using multiple imputation for missing trough BP data to assess the impact of LOCF methodology and drop-outs. Subgroup analyses such as age, gender, race, and other important baseline factors may be performed for primary and key secondary efficacy variables. Exploratory analyses on region or center effect may be performed for primary efficacy variables.

Population pharmacokinetic analyses will be explored. Plasma concentration of TAK-536, TAK-536 M-II, and chlorthalidone at different time points will be listed for each subject by treatment and dose level and analyzed using population pharmacokinetic modeling as appropriate and reported separately. The change from baseline in the biomarkers will be performed using ANCOVA with treatment as a fixed effect and the baseline value of the biomarker as a covariate.

Safety evaluation will include adverse events, clinical laboratory data, vital signs (including orthostatic vital signs), and electrocardiogram findings.

EXAMPLE 3

A Phase 3, Open-Label, Randomized, Long-Term Comparison of the Safety and Tolerability of the (5-methyl-2-oxo-1,3-dioxol-4-yl)methyl 2-ethoxy-1-{[2'45-oxo-4,5-dihydro-1,2,4-oxadiazol-3-yl)biphenyl-4-yl]methyl}-1H-benzimidazole-7-carboxylate potassium salt Plus Chlorthalidone Fixed-Dose Combination versus Benicar HCT® (Olmesartan Medoxomil-Hydrochlorothiazide) Fixed-Dose Combination in Subjects With Essential Hypertension Purpose The purpose of this study is to compare the safety and tolerability of (5-methyl-2-oxo-1,3-dioxol-4-yl)methyl 2-ethoxy-1-{[T-(5-oxo-4,5-dihydro-1,2,4-oxadiazol-3-yl)

biphenyl-4-yl]methyl}-1H-benzimidazole-7-carboxylate potassium salt plus chlorthalidone fixed-dose combination versus the olmesartan medoxomil-hydrochlorothiazide fixed-dose combination in subjects with essential hypertension. More specifically, this study is a phase 3, open-lable, randomized, long-term comparison of the safety and tolerability of the (5-methyl-2-oxo-1,3-dioxol-4-yl)methyl 2-ethoxy-1-{[2'-(5-oxo-4,5-dihydro-1,2,4-oxadiazol-3-yl) biphenyl-4-yl]methyl}-1H-benzimidazole-7-carboxylate potassium salt plus chlorthalidone fixed-dose combination versus the olmesartan medoxomil-hydrochlorothiazide fixed-dose combination in subjects with essential hypertension.

Number of Subjects: 400 to 440 per treatment group for a total of 800 to 880 subjects.

Number of Sites: Approximately 91 sites in United States and Canada and approximately 21 sites in Europe.

Route of Administration: Oral

Duration of Treatment: 1 year (52 weeks)

Period of Evaluation: 55 weeks

Primary Outcome Measures:
Evaluate the long-term safety and tolerability of the (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone fixed-dose combination in comparison to the Olmesartan Medoxomil-Hydrochlorothiazide fixed-dose combination in subjects with essential hypertension.

Percentage of subjects with adverse events (AE) from Week 0 to Week 52.

Secondary Outcome Measures:
Evaluate the long-term efficacy of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone fixed-dose combination in comparison to the Olmesartan-Medoxomil-Hydrochlorothiazide fixed-dose combination when using a titration to target treatment approach.

Percentage of subjects with serum creatinine elevations from baseline greater than 50% and greater than the upper limit of normal (ULN) from Week 0 to Week 52.

Change from baseline in sitting, clinic systolic blood pressure (SBP) and diastolic blood pressure (DBP) at each study visit.

Safety endpoints (clinical safety laboratory tests, 12-lead electrocardiogram (ECG) findings, and vital signs (including orthostatic vital signs)).

As mentioned briefly above, this study is being conducted to evaluate the safety and tolerability of (5-methyl-2-oxo-1, 3-dioxol-4-yl)methyl 2-ethoxy-1-{[2'-(5-oxo-4,5-dihydro-1, 2,4-oxadiazol-3-yl)biphenyl-4-yl]methyl}-1H-benzimidazole-7-carboxylate potassium salt in combination with chlorthalidone administered to subjects with uncontrolled hypertension compared to that of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt combined with chlorthalidone.

Individuals participating in this study were required to provide written informed consent. Study participation is anticipated to be about 52 Weeks.

| ELIGIBILITY | |
|---|---|
| Ages Eligible for Study: | 18 Years and older |
| Genders Eligible for Study: | Both |
| Healthy Volunteers Accepted: | No |

Criteria

Inclusion Criteria
  Is treated with antihypertensive therapy and has a post-washout mean sitting clinic SBP >160 and 190 mm Hg on Day 1 or has not received antihypertensive treatment since Day minus 14 and has a mean sitting clinic SBP≥160 and ≤190 mm Hg at the Screening Day and on Day 1.
  Females of childbearing potential who are sexually active must agree to use adequate contraception, and can neither be pregnant nor lactating from Screening throughout the duration of the study.
  Has clinical laboratory evaluations (including clinical chemistry, hematology, and complete urinalysis) within the reference range for the testing laboratory or results that are deemed not clinically significant for inclusion into this study by the investigator.
  Willing to discontinue current antihypertensive medications at the Screening Day minus 21 visit.

Exclusion Criteria
  Has sitting trough clinic diastolic blood pressure greater than 119 mmHg at Day 1.
  Is required to take or continues taking any disallowed medication, prescription medication, herbal treatment or over-the counter medication that may interfere with evaluation of the study medication, including:
    Antihypertensive agents except those used at the time of screening visit, which must be discontinued during the washout/run-in period and for the remainder of the study.
    Amlodipine should be discontinued at Screening Day-28; all other antihypertensive agents should be discontinued at Screening Day-21
    Insulin.
    Other agents that alter blood pressure, including:
      tricyclic antidepressants
      monoamine oxidase inhibitors
      lithium
      Phosphodiesterase type 5
      diet medications
      amphetamines or their derivatives
    chronically used (defined as more than 3 doses per week) common cold medications or non-steroidal anti-inflammatory drugs, including aspirin greater than 325 mg per day or cyclooxygenase-2 inhibitors
    Thiazolidinediones
    Atypical antipsychotic agents.
    Hypersensitive to AII receptor blockers, thiazide-type diuretics, or other sulfonamide-derived compounds.
  Recent history (within the last 6 months) of myocardial infarction, heart failure, unstable angina, coronary artery bypass graft, percutaneous coronary intervention, hypertensive encephalopathy, cerebrovascular accident, or transient ischemic attack.
  Clinically significant cardiac conduction defects (for example, 3rd degree atrioventricular block, left bundle branch block, sick sinus syndrome, atrial fibrillation).

Hemodynamically significant left ventricular outflow obstruction due to aortic valvular disease.

The subject has secondary hypertension of any etiology.

Severe renal dysfunction or disease (based on estimated glomerular filtration rate (GFR) less than 30 mL/min/1.73 m2) at Screening.

Known or suspected unilateral or bilateral renal artery stenosis.

History of drug abuse (defined as illicit drug use) or a history of alcohol abuse (defined as regular or daily consumption of more than 2 alcoholic drinks per day) within the past 2 years.

Previous history of cancer that has not been in remission for at least 5 years prior to the first dose of study drug. (This criterion does not apply to those subjects with basal cell or Stage 1 squamous cell carcinoma of the skin.)

Poorly-controlled type 1 or 2 diabetes mellitus (glycosylated hemoglobin greater than 8.0% at Screening).

Hypo- or hyperkalemia (defined as serum potassium outside of the normal reference range of the central laboratory) at Screening.

Alanine aminotransferase or aspartate aminotransferase level of greater than 2.5 times the upper limit of normal, active liver disease, or jaundice at Screening.

Currently is participating in another investigational study or has participated in an investigational study within 30 days prior to randomization.

Study site employee, or is an immediate family member (ie, spouse, parent, child, sibling) of a study site employee who is involved in conduct of this study.

Any other known serious disease or condition that would compromise subject safety, might affect life expectancy, or make it difficult to successfully manage and follow the subject according to the protocol.

Randomized/enrolled in a previous (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt or (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone study (this criterion does not apply to subjects who began participation in another (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt or (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone study but were not randomized, nor does it apply to subjects who participated in observational studies that lacked an intervention or invasive procedure).

Has a known hypersensitivity to angiotensin II receptor blockers or thiazide-type diuretics or other sulfonamide-derived compounds.

If female, is pregnant or lactating or intending to become pregnant before or during study participation, or within 30 days after last study drug dose.

As previously mentioned above, the purpose of this study is to compare the safety and tolerability of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone fixed-dose combination versus the olmesartan medoxomil-hydrochlorothiazide fixed-dose combination in subjects with essential hypertension. More specifically, this study is a phase 3, open-Table, randomized, long-term comparison of the safety and tolerability of the (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone fixed-dose combination versus the olmesartan medoxomil-hydrochlorothiazide fixed-dose combination in subjects with essential hypertension.

Eligible subjects who enroll in the study will be randomized in a 1:1 ratio to receive open-label treatment with either (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone or Olmesartan Medoxomil-Hydrochlorothiazide for up to 52 weeks. (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone may be titrated from an initial dose of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone 40 mg+12.5 mg on Day 1 to (5-methyl-2-oxo-1,3-dioxol-4-yl)methyl 2-ethoxy-1-{[2'-(5-oxo-4,5-dihydro-1,2,4-oxadiazol-3-yl) biphenyl-4-yl]methyl}-1H-benzimidazole-7-carboxylate potassium salt plus chlorthalidone 80 mg+12.5 mg at Week 4 (and throughout the remainder of the study) if needed to reach target blood pressure, up to a maximum dose of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone 80 mg+25 mg at Week 8 (and throughout the remainder of the study) if needed and if the maximum dose is reached, other antihypertensive treatments (except other angiotensin II receptor blockers or thiazide-type diuretics) can be added as needed at Week 12 (and throughout the remainder of the study), according to a titration-to-target blood pressure approach.

Subjects randomized to Olmesartan Medoxomil-Hydrochlorothiazide in North America may be titrated from an initial dose of Olmesartan Medoxomil 20 mg plus Hydrochlorothiazide 12.5 mg (20 mg+12.5 mg) on Day 1 to 40 mg+12.5 mg at Week 4 (and throughout the reaminder of the study) if needed to reach target blood pressure, up to a maximum dose of 40 mg+25 mg at Week 8 (and throughout the remainder of the study) if needed and, if maximum dose is reached, other antihypertensive treatments (except other angiotensin II receptor blockers or thiazide-type diuretics) may be added as needed at Week 12 (and throughout the remainder of the study), according to a titration-to-target approach.

Those subjects randomized to Olmesartan Medoxomil-Hydrochlorothiazide in Europe may be titrated from an initial dose of 20 mg+12.5 mg at Day 1 up to a maximum dose of 20 mg+25 mg at Week 4 (and throughout the remainder of the study) if needed to reach target blood pressure. If maximum dose is reached, other antihypertensive treatments (except other angiotensin II receptor blockers or thiazide-type diuretics) may be added as needed at Week 8 (and through the remainder of the study). After (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone or Olmesartan Medoxomil-Hydrochlorothiazide has been titrated to the maximum dose, other antihypertensive agents (with the exception of other angiotensin II receptor blockers or thiazide-type diuretics) may be added if needed to reach blood pressure targets. Target blood pressure is defined as <140/90 mm Hg for subjects without diabetes and without chronic kidney disease or <130/80 mm Hg for subjects with diabetes or chronic kidney disease (baseline estimated glomerular filtration rate <60 mL/min/1.73 m2), or urinary albumin: creatinine ration >200 mg/g at Screening. The decision to titrate study drug, as well as determination of subject eligibility at the beginning of the study, will be based on the mean of 3 sitting, trough, and clinic blood pressure measurements.

Sample Size Justification

There is no formal sample size justification in this study. Approximately 800 to 880 subjects will be enrolled, with at least 400 subjects per treatment group expected to complete 1-year (52 weeks) of treatment.

Statistical Considerations

Any subject who receives at least one dose of study medication will be included in summary statistics of safety and efficacy analysis. Descriptive statistics will be provided on primary, secondary, and other safety endpoints by treatment groups. Efficacy analyses will be performed on change from baseline for blood pressure (DBP and SBP) by treatment group and study visit. Subgroup analyses of race (black and non-black) and region (North America and Europe) will also be performed on primary and secondary endpoints as well as efficacy data. Additional analyses will be performed if necessary and appropriate.

Interim analyses may be performed prior to all subjects having completed the study. Since this study is an open-label study, the conduct of the study will not be affected by these interim analyses.

EXAMPLE 4

A Phase 3, Double-Blind, Randomized, Efficacy and Safety Study of the (5-methyl-2-oxo-1,3-dioxol-4-yl) methyl 2-ethoxy-1-{[2'45-oxo-4,5-dihydro-1,2,4-oxadiazol-3-yl)biphenyl-4-yl]methyl}-1H-benzimidazole-7-carboxylate potassium salt Plus Chlorthalidone Fixed-Dose Combination Compared With (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and Hydrochlorothiazide Coadministration Therapy in Subjects with Moderate to Severe Essential Hypertension Purpose This study is being conducted to compare the antihypertensive effect of chlorthalidone vs hydrochlorothiazide when each is used with (5-methyl-2-oxo-1,3-dioxol-4-yl)methyl 2-ethoxy-1-{[2'-(5-oxo-4,5-dihydro-1,2,4-oxadiazol-3-yl) biphenyl-4-yl]methyl}-1H-benzimidazole-7-carboxylate potassium salt in subjects with moderate to severe essential hypertension. More specifically, this study is a phase 3, double-blind, randomized, efficacy and safety study of the (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone fixed-dose combination compared with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and hydrochlorothiazide coadministration therapy in subjects with moderate to severe essential hypertension.

Number of Subjects: 300 to 330 per treatment group for a total of 600 to 660 subjects.

Number of Sites: Approximately 66 sites in United States and Russia.

Route of Administration: Oral

Duration of Treatment: Single-blind: 2 weeks; Double-blind: 8 weeks

Period of Evaluation: 7- to 14 day Screening period (a); 14-day single-blind placebo run-in period (a); 2-week single-blind treatment period; 8-week double-blind treatment period; 14-day follow-up period for adverse effects and concomitant medications; (a) coincides with a 3- to 4-week washout period.

Primary Outcome Measures:

Change from Baseline in trough, sitting, clinic Systolic Blood Pressure [Time Frame: Weeks 6 and 10]

Secondary Outcome Measures:

Change from Baseline in trough, sitting, clinic Diastolic Blood Pressure [Time Frame: Weeks 6 and 10]

Change from Baseline in mean trough Systolic Blood Pressure and Diastolic Blood Pressure (22 to 24 hours after dosing) per ambulatory blood pressure monitoring. [Time Frame: Weeks 6 and 10]

Change from Baseline in 24-hour mean Systolic. Blood Pressure and Diastolic Blood Pressure per ambulatory blood pressure monitoring. [Time Frame: Weeks 6 and 10]

Change from Baseline in the mean daytime (6 AM to 10 PM) Systolic Blood Pressure and Diastolic Blood Pressure per ambulatory blood pressure monitoring. [Time Frame: Weeks 6 and 10]

Change from baseline in the mean nighttime (12 AM to 6 AM) Systolic Blood Pressure and Diastolic Blood Pressure per ambulatory blood pressure monitoring. [Time Frame: Weeks 6 and 10]

Change from baseline in the mean Systolic Blood Pressure and Diastolic Blood Pressure at 0 to 12 hours after dosing per ambulatory blood pressure monitoring [Time Frame: Weeks 6 and 10]

Trough-to-Peak Ratio as determined by ambulatory blood pressure monitoring [Time Frame: Weeks 6 and 10]

Proportion of subjects who reached their trough, sitting, clinic Systolic and Diastolic blood pressure targets, defined as <140/90 mm Hg without diabetes or chronic kidney disease or <130/80 mm Hg with diabetes or chronic kidney disease [Time Frame: Weeks 2, 4, 6, 8 and 10]

Proportion of subjects who reached their trough, sitting, clinic Systolic blood pressure targets, defined as <140 mm Hg for subjects without diabetes or chronic kidney disease or <130 mm Hg for subjects with diabetes or chronic kidney disease [Time Frame: Weeks 2, 4, 6, 8 and 10]

Proportion of subjects who reached their trough, sitting, clinic Diastolic blood pressure targets, defined as <90 mm Hg for subjects without diabetes or chronic kidney disease or <80 mm Hg for subjects with diabetes or chronic kidney disease [Time Frame: Weeks 2, 4, 6, 8 and 10]

Time to achievement of trough, sitting, clinic Systolic and Diastolic blood pressure targets.

Time to achievement of trough, sitting, clinic Systolic blood pressure targets.

Time to achievement of trough, sitting, clinic Diastolic blood pressure targets.

Safety endpoints (adverse effects, safety laboratory tests, 12-lead electrocardiogram (ECG) findings, and vital signs (including orthostatic vital signs).

Doses and Titration Scheme:

| | Step 1 | | | Step 2 | |
|---|---|---|---|---|---|
| | Weeks 1-2 (Single-Blind) | Forced addition of chlorthalidone or hydrochlorothiazide | Weeks 3-6 (Double-Blind) | Doses of chlorthalidone or hydrochlorothiazide will be increased as needed to achieve target blood pressure | Weeks 7-10 (Double-Blind) |
| | (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone 40 mg + placebo mg | → | (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone 40 mg + 12.5 mg and hydrochlorothiazide placebo mg | → | (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone 40 mg + 25 mg and hydrochlorothiazide placebo mg |
| | (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone 40 mg + placebo mg | → | (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone 40 mg + placebo mg and hydrochlorothiazide 12.5 mg | → | (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone 40 mg + placebo mg and hydrochlorothiazide 25 mg |

As illustrated in the Doses and Titration Scheme Table, eligible subjects will receive single-blind treatment with (5-methyl-2-oxo-1,3-dioxol-4-yl)methyl 2-ethoxy-1-{[2'45-oxo-4,5-dihydro-1,2,4-oxadiazol-3-yl)biphenyl-4-yl]methyl}-1H-benzimidazole-7-carboxylate potassium salt 40 mg for 2 weeks as monotherapy. Double-blind treatment will begin at Week 2 and will consist of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus 12.5 mg of chlorthalidone or hydrochlorothiazide. For subjects who do not achieve the target blood pressure by Week 6, the dose of chlorthalidone or hydrochlorothiazide will be increased to 25 mg. If both target Systolic and Diastolic blood pressure are achieved by Week 6, the does of chlorthalidone or hydrochlorothiazide will remain at 12.5 mg for the duration of the study. Throughout the study, chlorthalidone (or matching placebo) will be administered in fixed dose combination with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt, whereas hydrochlorothiazide (or matching placebo) will be administered as an individual capsule.

Total commitment time for this study is about 13 weeks and each subject will be contacted by telephone 14 days after the last dose of study drug for a follow-up adverse event and concomitant medication assessment. Subjects are being required to wear a blood pressure monitor for three 24-hour periods during the study. The baseline recording will begin on Day-1. One interim ambulatory blood pressure monitoring recording will be conducted after administration of study drug at Week 6 (before any subjects have their chlorthalidone or hydrochlorothiazide dose increased), and the final recording will begin after administration of the last dose of treatment at the Week 10 Visit. Trough, sitting, clinic blood pressure readings will be administered at each visit. Standing blood pressure and pulse will also be measured at each study visit to evaluate orthostatic vital signs.

Eligibility

| Ages Eligible for Study: | 18 Years and older |
|---|---|
| Genders Eligible for Study: | Both |
| Healthy Volunteers Accepted: | No |

Criteria

Inclusion Criteria

Is treated with antihypertensive therapy and has a post-washout mean sitting clinic SBP greater than or equal to 160 and less than or equal to 190 mm Hg on Day-1; or the subject has not received antihypertensive treatment within 28 days prior to Screening and has a mean sitting clinic SBP greater than or equal to 160 and less than or equal to 190 mm Hg at the Screening Visit and on Day-1.

Females of childbearing potential who are sexually active agree to routinely use adequate contraception from Screening through 30 days after the last administered study drug dose.

Has clinical laboratory test results (clinical chemistry, hematology, and complete urinalysis) within the reference range for the testing laboratory or the investigator does not consider the results to be clinically significant.

Is willing to discontinue current antihypertensive medications on Day-21 or Day-28 if the subject is on amlodipine or chlorthalidone.

Exclusion Criteria

Has a mean sitting clinic diastolic blood pressure greater than 119 mm Hg on Day-1.

Has a baseline 24-hour ambulatory blood pressure monitoring reading of insufficient quality.

Works a night (third) shift (defined as 11 PM [2300] to 7 AM [0700]).

Has an upper arm circumference less than 24 cm or greater than 42 cm.

Is noncompliant (less than 70% or greater than 130%) with study medication during the placebo run-in period.

Has secondary hypertension of any etiology (eg, renovascular disease, pheochromocytoma, Cushing's syndrome).

Has a recent history (within the last 6 months) of myocardial infarction, heart failure, unstable angina, coronary artery bypass graft, percutaneous coronary intervention, hypertensive encephalopathy, cerebrovascular accident, or transient ischemic attack.

Has clinically significant cardiac conduction defects (ie, third-degree atrioventricular block, sick sinus syndrome, atrial fibrillation, or atrial flutter).

Has hemodynamically significant left ventricular outflow obstruction due to aortic valvular disease.

Has severe renal dysfunction or disease [based on estimated glomerular filtration rate less than 30 mL/min/1.73 m2 at Screening].

Has known or suspected unilateral or bilateral renal artery stenosis.

Has a history of cancer that has not been in remission for at least 5 years prior to the first dose of study drug. (This criterion does not apply to those subjects with basal cell or stage I squamous cell carcinoma of the skin).

Has poorly-controlled type 1 or type 2 diabetes mellitus (hemoglobin A1c >8.0%) at Screening.

Has hypokalemia or hyperkalemia (defined as serum potassium outside of the normal reference range of the central laboratory).

Has an alanine aminotransferase or aspartate aminotransferase level of greater than 2.5 times the upper limit of normal, active liver disease, or jaundice.

Has known hypersensitivity to angiotensin II receptor blockers or thiazide-type diuretics or other sulfonamide-derived compounds.

If female, the subject is pregnant or lactating or intending to become pregnant before or during study participation, or within 30 days after last administered study drug dose.

Sample Size Justification

Assuming a standard deviation (SD) of 14 mm Hg and a 15% dropout rate, a total of 600 enrolled subjects (300 per treatment group) is sufficient to achieve about 90% power to detect a difference of 4 mm Hg between chlorthalidone and hydrochlorothiazide when each is administered in combination with (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt by a 2-sample t-test of the mean change from baseline in trough, sitting, clinic SBP with a two-sided significance level of 5%.

Statistical Considerations

The primary efficacy variable will be change from baseline to Weeks 6 and 10 in trough, sitting, clinic SBP. The primary analyses will be based on an analysis of covariance (ANCOVA) model for change from baseline to Weeks 6 and 10 for the primary efficacy variable. The model will include treatment as a factor and its baseline as covariate. The P-value and 2-sided 95% confidence interval of treatment difference in change from baseline will be provided. Type I error will be controlled using a stepwise testing procedure. The first treatment test will be done at Week 6. If it is statistically insignificant at a significance level of 5%, then the treatment comparison at Week 10 will be performed.

The secondary efficacy variables will include change from baseline to Weeks 6 and 10 in trough, sitting, clinic DBP; 24-hour mean SBP and DBP by ambulatory blood pressure monitoring parameters for SBP and DBP; and blood pressure response rates.

An analysis will be performed on change from baseline to Weeks 6 and 10 in mean trough, sitting, clinic DBP with treatment as a fixed effect and its baseline as covariate. These analyses will also be performed on 24-hour mean SBP and DBP by ambulatory blood pressure monitoring and other ambulatory blood pressure monitoring parameters for SBP and DBP. The trough-to-peak ratio at Weeks 6 and 10 will also be calculated and summarized. Similar analyses on trough, sitting, clinic SBP and DBP will also be conducted at each other scheduled visit where clinic blood pressure is recorded.

The exploratory efficacy variables are time from randomization to the first achievement of target trough, sitting, clinic SBP and target trough, sitting, clinic DBP; time from randomization to the first achievement of target trough, sitting, clinic SBP; time from randomization to the first achievement of target trough, sitting, clinic DBP.

For the time from randomization to the first achievement of target trough, sitting, clinic SBP and target trough, sitting, clinic DBP, subjects who have not reached the target SBP or target DBP at the end of the study will be censored as of the date the subject was last known to be above the target SBP or DBP. This analysis will be performed using the stratified log-rank test to determine whether the time to target clinical SBP and target clinical DBP is shorter in (5-methyl-2-oxo-1,3-dioxol-4-yl)methyl 2-ethoxy-1-{[2'45-oxo-4,5-dihydro-1,2,4-oxadiazol-3-yl)biphenyl-4-yl]methyl}-1H-benzimidazole-7-carboxylate potassium salt plus chlorthalidone than in (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus hydrochlorothiazide. The stratification factor will be race (black versus non-black). The product limit (Kaplan-Meier) estimates for the survival of the two treatment groups will be plotted. Similar analyses will be performed for time from randomization to the first achievement of target trough, sitting, clinic SBP and time from randomization to the first achievement of target trough, sitting, clinic DBP.

A logistic model with treatment as a fixed effect and baseline clinic SBP as a covariate will be used to analyze the response criteria for clinic SBP for each clinic visit. The odds ratio and its 95% confidence interval will be estimated. Similar models will be used to analyze the response criteria for clinic DBP with baseline clinic DBP as a covariate and the joint response criteria for both clinic SBP and DBP with baseline clinic SBP as a covariate.

The ANCOVA for the clinic SBP and DBP will be performed on Last Observation Carried Forward (LOCF) data set. In the LOCF analysis data set, the last post-baseline observed value will be carried forward and used for all subsequent scheduled time points where data are missing (e.g., the subject has missing data or has dropped out of the study). The efficacy analysis for the response criteria will also be based on the LOCF data set. Sensitivity analyses on trough clinic SBP and DBP will be performed on observed values and using multiple imputation for missing trough clinic BP data to assess the impact of LOCF methodology and dropouts.

Additional analyses may be performed for subgroups based on age, gender, race, and other important baseline factors if needed. Exploratory analyses on region or center effect may also be performed if possible.

Biomarker Analysis

Secondary analyses will be performed on the change from baseline in the biomarkers using treatment as a fixed effect and the baseline value of the biomarker as a covariate.

Safety Analysis

All safety assessments, including AEs, clinical laboratory test results, vital sign measurements, and 12-lead ECG results will be presented in the data listings. Treatment-emergent AEs will be summarized by treatment group. Laboratory values, pulse rate, and 12-lead ECG results will be summarized with descriptive statistics and/or shift tables.

EXAMPLE 5

A Phase 3, Double-Blind, Randomized, Efficacy and Safety Study Comparing the (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt Plus Chlorthalidone Fixed-Dose Combination versus Benicar HCT® (Olmesartan Medoxomil-Hydrochlorothiazide) in Subjects With Moderate to Severe Essential Hypertension Purpose This study is being conducted to determine the efficacy and safety of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt combined with chlorthalidone in subjects with moderate to severe essential hypertension. More specifically, this study a phase 3, double-blind, randomized, efficacy and safety study comparing the (5-methyl-2-oxo-1,3-dioxol-4-yl)methyl 2-ethoxy-1-{[2'-(5-oxo-4,5-dihydro-1,2,4-oxadiazol-3-yl) biphenyl-4-yl]methyl}-1H-benzimidazole-7-carboxylate potassium salt plus chlorthalidone fixed-dose combination versus Benicar HCT® (Olmesartan Medoxomil-Hydrochlorothiazide),in subjects with moderate to severe essential hypertension.

Number of Subjects: 370 to 407 per treatment group for a total of 1110 to 1221 subjects.
Number of Sites: Approximately 150 sites in United States and Central/South America.
Route of Administration: Oral
Duration of Treatment: 8 weeks
Period of Evaluation: 12 weeks.

Primary Outcome Measures:
Change from Baseline in mean trough, sitting, clinic Systolic Blood Pressure. [Time Frame: Baseline and Week 8]

Secondary Outcome Measures:
Change from Baseline in mean trough, sitting, clinic Systolic Blood Pressure. [Time Frame: Week 4]
Change from Baseline in trough, sitting, clinic Diastolic Blood Pressure [Time Frame: Weeks 4 and 8]
Change from Baseline in mean trough Systolic Blood Pressure and Diastolic Blood Pressure through ambulatory blood pressure monitoring (22 to 24 hours after dosing). [Time Frame: Weeks 4 and 8]
Change from Baseline in 24-hour mean Systolic Blood Pressure and Diastolic Blood Pressure through ambulatory blood pressure monitoring. [Time Frame: Weeks 4 and 8]
Change from Baseline in mean daytime (6 AM to 10 PM) Systolic Blood Pressure and Diastolic Blood Pressure through ambulatory blood pressure monitoring. [Time Frame: Weeks 4 and 8 ]
Change from Baseline in mean nighttime (12 AM to 6 AM) Systolic Blood Pressure and Diastolic Blood Pressure through ambulatory blood pressure monitoring. [Time Frame: Weeks 4 and 8]
Change from Baseline in mean Systolic Blood Pressure and Diastolic Blood Pressure at 0 to 12 hours after dosing through ambulatory blood pressure monitoring. [Time Frame: Weeks 4 and 8 ]
Proportion of subjects who reached their Systolic and Diastolic blood pressure targets, defined as <140/90 mm Hg for subjects without diabetes or chronic kidney disease (CKD) or <130/80 mm Hg for subjects with diabetes or CKD (estimated GFR<60 mL/min/1.73 m² or urinary albumin:creatinine ratio>200 mg albumin/g creatinine at Screening) [Time Frame: Weeks 2, 4, 6 and Week 8]
Proportion of subjects who reached their Systolic blood pressure targets, defined as defined as <140 mm Hg for subjects without diabetes or chronic kidney disease (CKD) or <130 mm Hg for subjects with diabetes or CKD [Time Frame: Weeks 2, 4, 6 and Week 8 ]
Proportion of subjects who reached their Diastolic blood pressure targets, defined as defined as <90 mm Hg for subjects without diabetes or CKD or 80 mm Hg for subjects with diabetes or CKD [Time Frame: Weeks 2, 4, 6 and Week 8 ]
Time to achievement of target Systolic blood pressure and Diastolic blood pressure (trough, sitting, clinic)
Time to achievement of target Systolic blood pressure (trough, sitting, clinic)
Time to achievement of target Diastolic blood pressure (trough, sitting, clinic)
Safety endpoints (adverse effects, safety laboratory tests, 12-lead electrocardiogram (ECG) findings, and vital signs (including orthostatic vital signs).

Eligible subjects will be randomly assigned to 8 weeks of treatment with one of the combination treatment regimens listed below. For subjects who do not achieve their target SBP and DBP by Week 4, study drug will be increased (titrated) to a higher dose. Subjects who achieve both blood pressure targets by Week 4 will continue to receive their starting dose for the remainder of the study. BP target is defined as <140/90 mm Hg for subjects without diabetes or chronic kidney disease (CKD) or <130/80 mm Hg for subjects with diabetes or CKD. The decision to titrate study drug at Week 4, as well as subject eligibility at the beginning of the study, will be based on the mean of 3 sitting, trough, clinic blood pressure measurements.

| Randomization Group | Week 4 | Remainder of Study |
|---|---|---|
| 1: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 20 mg and chlorthalidone 12.5 mg, tablets, orally (20 mg + 12.5 mg) | If participant does not achieve target blood pressure | Dosage increased to (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg and chlorthalidone 25 mg, tablets (40 mg + 25 mg), orally, once daily for the remainder of the study. |
|  | If participant does achieve target blood pressure | Initial dose unchanged for the remainder of the study |
| 2: (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 40 mg and chlorthalidone 12.5, mg, tablets, orally (40 mg + 12.5 mg) | If participant does not achieve target blood pressure | Dosage increased to (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt 80 mg and chlorthalidone 25 mg (80 mg + 25 mg), orally, once daily for the remainder of the study. |
|  | If participant does achieve target blood pressure | Initial dose unchanged for the remainder of the study |
| 3: Olmesartan medoxomil 20 mg/hydrochlorothiazide 12.5 mg, capsules, orally (20 mg + 12.5 mg) | If participant does not achieve target blood pressure | Dosage increased to olmesartan medoxomil 40 mg/hydrochlorothiazide 25 mg, capsule (40 mg + 25 mg), orally, once daily for the remainder of the study. |
|  | If participant does achieve target blood pressure | Initial dose unchanged for the remainder of the study |

Sitting and standing, trough clinic blood pressure readings and pulse measurements will be measured in the clinic throughout the study. 24-hour ambulatory blood pressure monitoring will be conducted three times. Subjects are required to have a baseline (Day-1) ambulatory blood pressure monitoring reading that meets predefined quality control criteria in order to be eligible for Randomization. The interim ambulatory blood pressure monitoring will begin at the Week 4 visit, and the final ambulatory blood pressure monitoring will begin at the Week 8 visit. The total duration of the study is approximately 12 weeks. Participants will make a total of 11 visits to the clinic, and are required to participate in a follow-up telephone call 14 days after last dose of the study drug for adverse event assessment and concomitant medication assessment.

Eligibility

| Ages Eligible for Study: | 18 Years and older |
|---|---|
| Genders Eligible for Study: | Both |
| Healthy Volunteers Accepted: | No |

Criteria

Inclusion Criteria

Is treated with antihypertensive therapy and has a post-washout mean sitting clinic systolic blood pressure greater than or equal to 160 and less than or equal to 190 mm Hg on Day-1 or if the subject has not received antihypertensive treatment within 28 days before screening and has a mean sitting clinic systolic blood pressure greater than or equal to 160 and less than or equal to 190 mm Hg at the Screening Visit and on Day-1.

Females of childbearing potential who are sexually active must agree to use adequate contraception, and can neither be pregnant nor lactating from Screening throughout the duration of the study.

Has clinical laboratory test results within the reference range for the testing laboratory or the investigator does not consider the results to be clinically significant.

Is willing to discontinue current antihypertensive medications on Day-21 or on Day-28 if Has is on amlodipine or chlorthalidone.

Exclusion Criteria

Has a mean sitting clinic diastolic blood pressure greater than 119 mm Hg on Day Has a baseline 24-hour ambulatory blood pressure monitoring reading of insufficient quality.

Works a night (third) shift (from 11 PM [2300] to 7 AM [0700]).

Has an upper arm circumference less than 24 cm or greater than 42 cm.

Is noncompliant (<70% or >130%) with study medication during the placebo run-in period.

Has secondary hypertension of any etiology.

Has a recent history (within the last 6 months) of myocardial infarction, heart failure, unstable angina, coronary artery bypass graft, percutaneous coronary intervention, hypertensive encephalopathy, cerebrovascular accident or transient ischemic attack.

Has a clinically significant cardiac conduction (i.e. third-degree atrioventricular bock, sick sinus syndrome, atrial fibrillation, or atrial flutter).

Has hemodynamically significant left ventricular outflow obstruction due to aortic valvular disease.

Has severe renal dysfunction or disease (based on glomerular filtration rate [GFR]<30 mL/min/1.73 m$^2$ at Screening).

Has a known or suspected unilateral or bilateral renal artery stenosis.

Has a history of cancer that has not been in remission for at least 5 years prior to the first dose of study drug. (This criterion does not apply to those subjects with basal cell or stage I squamous cell carcinoma of the skin.).

Has poorly controlled type 1 or type 2 diabetes mellitus (hemoglobin Alc>8.0% at Screening).

Has hypokalemia or hyperkalemia (defined as serum potassium outside of the normal reference range of the central laboratory).

Has an alanine aminotransferase or aspartate aminotransferase level of greater than 2.5 times the upper limit of normal, active liver disease or jaundice.

Has a known hypersensitivity to angiotensin II receptor blockers or thiazide-type diuretics or other sulfonamide-derived compounds.

If female, the subject is pregnant or lactating or intending to become pregnant before or during study participation, or within 30 days after last study drug dose.

As mentioned briefly above, the purpose of this study is to determine the efficacy and safety of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt combined with chlorthalidone in subjects with moderate to severe essential hypertension. Subjects participating in this study have been randomized to receive one of 3 possible dosing combinations of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt with either chlorthalidone or olmesartan medoxomil-hydrochlorothiazide over 8 weeks.

Sample Size Justification:

Assuming a standard deviation (SD) of 14.5 mm Hg and a 15% dropout rate, a total of 1110 enrolled subjects (370 per treatment group) is sufficient to achieve about 90% power to detect a difference of 3.75 mm Hg between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone and olmesartan medoxomil-hydrochlorothiazide by a 2-sample t-test of the mean change from baseline in trough, sitting, clinic SBP with a two-sided significance level of 5%. With the above assumed SD and treatment difference, this sample size also provides at least 90% power for demonstrating non-inferiority with a margin of 3.5 mm Hg between (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone and olmesartan medoxomil-hydrochlorothiazide for the primary endpoint.

Statistical Considerations

The primary efficacy variable will be change from baseline at Week 8 in trough, sitting, clinic SBP. The primary analysis will be based on an analysis of covariance (ANCOVA) model for change from baseline to final visit for the primary efficacy variable. The model will include treatment as a factor and its baseline as covariate. The P-value and 2-sided 95% confidence interval (CI) of treatment difference in change from baseline will be determined from the ANCOVA framework.

In an 8-week factorial study of olmesartan medoxomil-hydrochlorothiazide [33], placebo effect for clinic SBP was −3.3 mm Hg with a 2-sided 95% CI of (−6.8, −0.3), while the change from baseline in clinic SBP for 20 mg/25 mg was −27.1 mm Hg with a 2-sided 95% CI of (−30.0, −24.2) and the change from baseline in clinic SBP for 40 mg/25 mg was −26.8 mm Hg with a 2-sided 95% CI of (−30.8, −22.8). Therefore, the derived placebo-corrected treatment effect (95% CI) for clinic SBP for doses of 20 mg/25 mg and 40 mg/25 mg were about −23.8 (−28.2, −19.4) mm Hg and −23.5 (−28.7, −18.4) mm Hg, respectively. Thus, a non-inferiority margin of 3.5 mm Hg was selected in this study. Such a margin is about 15% of the observed SBP reduction for olmesartan medoxomil-hydrochlorothiazide.

A test of non-inferiority will be performed by comparing the upper-limit of the 95% CI of the treatment difference (i.e., (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone and olmesartan medoxomil-hydrochlorothiazide) to the value of 3.5 mm Hg; if this upper-limit is 3.5 mm Hg then (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone will be determined to be non-inferior to olmesartan medoxomil-hydrochlorothiazide.

The overall 2-sided type I error rate of 0.05 will be controlled using the stepwise testing procedure presented below.

Step 1: Comparing (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone high dose (40 mg+12.5 mg/80 mg+25 mg) versus olmesartan medoxomil-hydrochlorothiazide for non-inferiority. If (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone high dose is determined to be non-inferior to olmesartan medoxomil-hydrochlorothiazide then proceed to Step 2.

Step 2: Comparing (5-methyl-2-oxo-1,3-dioxol-4-yl)methyl 2-ethoxy-1-{[T-(5-oxo-4,5-dihydro-1,2,4-oxadiazol-3-yl)biphenyl-4-yl]methyl}-1H-benzimidazole-7-carboxylate potassium salt plus chlorthalidone high dose versus olmesartan medoxomil-hydrochlorothiazide for superiority. If the 2-sided P-value from the above ANCOVA for testing the 2 treatments is 0.05 then (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone high dose will be determined to be superior to olmesartan medoxomil-hydrochlorothiazide, and then proceed to Step 3.

Step 3: Comparing (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone low dose (20 mg+12.5 mg/40 mg+25 mg) versus olmesartan medoxomil-hydrochlorothiazide for non-inferiority. If (5-methyl-2-oxo-1,3-dioxol-4-yl)methyl 2-ethoxy-1-(1-{[2'-(5-oxo-4,5-dihydro-1,2,4-oxadiazol-3-yl)biphenyl-4-yl]methyl}-1H-benzimidazole-7-carboxylate potassium salt plus chlorthalidone low dose is determined to be non-inferior to olmesartan medoxomil-hydrochlorothiazide then proceed to Step 4.

Step 4: Comparing (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone low dose versus olmesartan medoxomil-hydrochlorothiazide for superiority. If the 2-sided P-value from the above ANCOVA for testing the 2 treatments is 0.05 then (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone low dose will be determined to be superior to olmesartan medoxomil-hydrochlorothiazide.

The key secondary endpoint (change from baseline at Week 4 in trough clinic sitting SBP) will be analyzed in a similar manner including the same stepwise testing procedure for controlling the type I error. Other secondary efficacy variables will include change from baseline in trough, sitting, clinic DBP; 24-hour mean SBP and DBP by ambulatory blood pressure monitoring parameters for SBP and DBP; other ambulatory blood pressure monitoring parameters for SBP and DBP; and blood pressure response rates.

An analysis will be performed on change from baseline to Weeks 4 and 8 in trough clinic sitting DBP with treatment as a fixed effect and its baseline as covariate.

The exploratory efficacy variables are time from randomization to the first achievement of target trough clinic sitting SBP and target trough clinic sitting DBP; time from randomization to the first achievement of target trough, sitting, clinic SBP; time from randomization to the first achievement of target trough, sitting, clinic DBP.

For the time from randomization to the first achievement of target trough, sitting, clinic SBP and target trough, sitting, clinic DBP, subjects who have not reached the target SBP or target DBP at the end of the study will be censored as of the date the subject was last known to be above the target SBP or DBP. Subjects who are known to have reached the target SBP and target DBP will be included in the analysis. Subjects with missing SBP or missing DBP at the end of the study will be censored as of the date the subject was last known to be above the target SBP or DBP. This analysis will be performed using the stratified log-rank test to determine whether the time to target clinical SBP and target clinical DBP is shorter in (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt plus chlorthalidone fixed-dose combination than with the olmesartan medoxomil-hydrochlorothiazide fixed-dose combination. The stratification factor will be race (black versus non-black). The product limit (Kaplan-Meier) estimates for the survival of the three treatment groups will be plotted. Similar analyses will be performed for time from randomization to the first achievement of target trough, sitting, clinic SBP and time from randomization to the first achievement of target trough, sitting, clinic DBP.

A logistic model with treatment as a fixed effect and baseline clinic SBP as a covariate will be used to analyze the response criteria for clinic SBP for each clinic visit. The odds ratio and its 95% confidence interval will be estimated. Similar models will be used to analyze the response criteria for clinic DBP with baseline clinic, DBP as a covariate and the joint response criteria for both clinic SBP and DBP with baseline clinic SBP as a covariate.

The efficacy analysis will be performed on Last Observation Carried Forward (LOCF) data set. In the LOCF analysis data set, the last post-baseline observed value will be carried forward and used for all subsequent scheduled time points where data are missing (e.g., the subject has missing data or has dropped out of the study). The efficacy analysis for the response criteria will also be based on the LOCF data set. Sensitivity analyses on trough clinic SBP and DBP will be performed on observed values and using multiple imputation for missing trough clinic BP data to assess the impact of LOCF methodology and drop-outs.

Additional analyses may be performed for subgroups based on age, gender, race, and other important baseline factors if needed. Exploratory analyses on region or center effect may also be performed if possible.

Biomarker Analysis

Analyses will be performed on the change from baseline in the biomarkers using treatment as a fixed effect and the baseline value of the biomarker as a covariate.

Safety Analysis

All safety assessments, including AEs, clinical laboratory test results, vital sign measurements, and 12-lead ECG results will be presented in the data listings. Treatment-emergent AEs will be summarized by treatment group. Laboratory values, pulse rate, and 12-lead ECG results will be summarized with descriptive statistics and/or shift tables.

EXAMPLE 6

A Phase 3, Double-Blind, Randomized, Efficacy and Safety Study Comparing Azilsartan Medoxomil Plus Chlorthalidone Fixed-Dose Combination in Subjects with Stage 2 Hypertension—A Summary of the Results of the Study Described in Example 1

The effects of azilsartan medoxomil (AZL-M) coadministered with chlorthalidone (CLD) in patients with stage 2 hypertension was studied as described in Example 1. This Example summarizes the results of the study from Example 1.

As discussed in Example 1, azilsartan medoxomil 40 or 80 mg plus chlorthalidone 25 mg versus placebo plus chlorthalidone 25 mg once daily was studied in a randomized double-blind trial using ambulatory blood pressure (BP) monitoring (ABPM) and clinic monitoring. The primary efficacy endpoint was change from baseline in 24-hour mean systolic BP(SBP) by ambulatory blood pressure monitoring. Patients (n=551) were randomized on the basis of clinic SBP≥160 and ≤190 mm Hg and 24-hour mean SBP≥140 and ≤180 mm Hg.

Baseline and 6-week ambulatory blood pressure monitoring data were available for 448 patients (mean age 59 yrs, 52% men, 16% African-American based on randomized subjects). Baseline 24-hour mean SBPs were similar in each group (Table 1). Azilsartan medoxomil 40 and 80 mg plus chlorthalidone 25 mg lowered 24-hour mean SBP more than chlorthalidone 25 mg plus placebo (Table 1). Absolute reductions in clinic SBP were significantly larger with azilsartan medoxomil 40 or 80 mg plus chlorthalidone 25 mg (−36.2 or −34.4 mm Hg, respectively) than with chlorthalidone plus placebo (−21.8 mm Hg). Hypotension and serum creatinine elevations were more frequent with chlorthalidone 25 mg plus azilsartan medoxomil than with chlorthiadone alone and reversed with drug discontinuation. Hypokalemia was more frequent with chlorthalidone plus placebo than with chlorthalidone plus azilsartan medoxomil.

Conclusion: The addition of azilsartan medoxomil to chlorthalidone substantially reduced clinic and 24-hour SBP in patients with stage 2 hypertension. Azilsartan medoxomil attenuated the hypokalemia seen with chlorthalidone alone. Reversible creatinine elevations with azilsartan medoxomil+ chlorthalidone 25 mg corresponded with potent BP reduction in a small proportion of patients and were consistent with the prolonged diuretic effect of chlorthalidone and renin-angiotensin blockade due to azilsartan medoxomil.

TABLE 1

Change from Baseline in Mean 24-Hour SBP by ABPM

| | | Chlorthalidone 25 mg + | |
| --- | --- | --- | --- |
| Measure | Placebo N = 181 | Azilsartan Medoxomil 40 mg N = 184 | Azilsartan Medoxomil 80 mg N = 182 |
| n (%) | 152 (84) | 149 (81) | 147 (81) |
| Baseline, mean ± SE (mm Hg) | 153.4 ± 0.8 | 152.0 ± 0.8 | 151.9 ± 0.8 |
| Δ from baseline, mean (mm Hg) | | | |
| Absolute | −15.9 | −31.7 | −31.3 |
| Placebo subtracted | | −15.9 | −15.5 |
| (95% CI) | | (−18.5, −13.2) | (−18.1, −12.8) |
| P value versus placebo | | <0.001 | <0.001 |

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A method of treating hypertension and reducing incidence of hypokalemia in a patient in need of treatment thereof, the method comprising the steps of:
    administering to said patient (5-methyl-2-oxo-1,3-dioxol-4-yl)methyl 2-ethoxy-1-{[2'-(5-oxo-4,5-dihydro-1,2,4oxadiazol-3-yl)biphenyl-4-yl]methyl}-1H-benzimidazole-7-carboxylate potassium salt in an amount selected from the group consisting of about 40 mg per day and about 80 mg per day, and chlorthalidone in an amount selected from the group consisting of about 12.5 mg per day and 25.0 mg per day, wherein the hypokalemia is greater than the reduction in incidence of hypokalemia is lower than the incidence of hypokalemia provided by 12.5 mg or 25.0 mg per day of chlorthalidone alone.

2. The method of claim 1, wherein the hypertension is essential hypertension, secondary hypertension, arterial hypertension, pulmonary arterial hypertension or portal vein hypertension.

3. The method of claim 1, wherein the benzimidazole derivative and chlorthalidone are administered as separate dosage forms.

4. The method of claim 3, wherein the benzimidazole derivative is administered as a tablet.

5. The method of claim 3, wherein the chlorthalidone is administered as a tablet.

6. The method of claim 1, wherein the benzimidazole derivative and chlorthalidone are administered together in a single dosage form.

7. The method of claim 6, wherein the single dosage form is a tablet.

* * * * *